(12) United States Patent
Mundy et al.

(10) Patent No.: US 7,211,252 B2
(45) Date of Patent: May 1, 2007

(54) METHODS OF TREATING MULTIPLE MYELOMA AND MYELOMA-INDUCED BONE RESORPTION USING INTEGRIN ANTAGONISTS

(75) Inventors: Gregory R. Mundy, San Antonio, TX (US); Toshiyuki Yoneda, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 35 days.

(21) Appl. No.: 09/805,840

(22) Filed: Mar. 13, 2001

(65) Prior Publication Data
US 2002/0022028 A1 Feb. 21, 2002

Related U.S. Application Data

(63) Continuation of application No. PCT/US99/21170, filed on Sep. 13, 1999.

(60) Provisional application No. 60/100,182, filed on Sep. 14, 1998.

(51) Int. Cl.
*A61K 39/395* (2006.01)
(52) U.S. Cl. .................................. 424/133.1; 424/143.1
(58) Field of Classification Search ............. 424/130.1, 424/133.1, 143.1, 93.7; 530/388.1, 388.22, 530/388.7
See application file for complete search history.

(56) References Cited

U.S. PATENT DOCUMENTS

| | | | |
|---|---|---|---|
| 5,217,870 A | 6/1993 | Hession et al. |
| 5,272,263 A | 12/1993 | Hession et al. |
| 5,367,056 A | 11/1994 | Hession et al. |
| 5,510,332 A | 4/1996 | Kogan et al. |
| 5,695,755 A | 12/1997 | Papayannopoulou |
| 5,824,304 A | 10/1998 | Papayannopoulou |
| 5,840,299 A | 11/1998 | Bendig |
| 5,843,438 A | 12/1998 | Papayannopoulou |
| 5,871,734 A | 2/1999 | Lobb et al. |
| 5,885,786 A | 3/1999 | Cabot |
| 5,888,507 A | 3/1999 | Burkly |
| 5,932,214 A | 8/1999 | Lobb et al. |
| 6,252,043 B1 | 6/2001 | Hession et al. |
| 6,307,025 B1 | 10/2001 | Hession et al. |
| 6,602,503 B1 | 8/2003 | Lobb et al. |
| 6,632,927 B2 | 10/2003 | Adair et al. |
| 6,692,742 B1 | 2/2004 | Nakamura |

FOREIGN PATENT DOCUMENTS

| | | |
|---|---|---|
| WO | WO 90/13300 | 11/1990 |
| WO | WO 93/13798 | 7/1993 |
| WO | WO 93/15764 | 8/1993 |
| WO | WO 94/11027 | 5/1994 |
| WO | WO 94/16094 | 7/1994 |
| WO | WO 94/17828 | 8/1994 |
| WO | WO 95/19790 | * 7/1995 |
| WO | WO 97/49428 | 12/1997 |
| WO | WO 99/61421 | 12/1999 |

OTHER PUBLICATIONS

Lokhorst HM, et al Primary tumor cells of myeloma patients induce interleukin-6 secretion in long-term bone marrow cultures. Blood. 84(7):2269-77, 1994.* van Zaanen HC, et al Chimaeric anti-interleukin 6 monoclonal antibodies in the treatment of advanced multiple myeloma: a phase I dose-escalating study. Br J Haematol.;102(3):783-90, Aug. 1998.*

Los Alamos National Laboratory web page: http://www.hiv.lanl.gov/content/immunology/ab_search?action=results;ab_id=706.*

Nishinarita et al., "Expression of $\beta_1$ Integrins (Very Late Antigens-4 and -5) on Myeloma Cells and Clinical Correlates in Patients with Multiple Myeloma." *The Journal of International Medical Research*, vol. 26, No. 1, pp. 37-42 (Jan./Feb. 1998).

Rodman, "Mechanisms of Bone Lesions in Multiple Myeloma and Lymphoma." *Cancer Supplement*, vol. 80, No. 8, pp. 1557-1563 (Oct. 15, 1997).

Vidriales, et al., "Adhesion of multiple myeloma cells to the bone marrow microenvironment: implications for future therapeutic strategies." *Molecular Medicine Today*, vol. 2, pp. 425-431 (Oct. 1996).

Akatsu et al., "Chinese Hamster Ovary Cells Expressing $\alpha_4\beta_1$ Integrin Stimulate Osteoclast Formation In Vitro." *Journal of Bone and Mineral Research*, vol. 13, No. 8, pp. 1251-1259 (1998).

Barker et al., "The Role of Adhesion Molecules in Multiple Myeloma." *Leukemia and Lymphoma*, vol. 8, pp. 189-196 (1992).

Cook et al., "The Role of Adhesion Molecules in Multiple Myeloma." *Acta Hæmatologica*; pp. 81-89 (1997).

Fehlner-Gardiner et al., "Differential utilization of VLA-4 ($\alpha 4\beta 1$) and 15($\alpha 5\beta 1$) integrins during the development of mouse bone marrow-derived mast cells." *Differentiation*, vol. 60, No. 4, pp. 317-325 (Jul. 1996).

Masellis-Smith et al., "Adhesion of Multiple Myeloma Peripheral Blood B Cells to Bone Marrow Fibroblasts: A Requirement for CD44 and $\alpha_4\beta 7^1$." *Cancer Research*, vol. 57, No. 5, pp. 930-936 (Mar. 1, 1997).

Michigami et al., "Interactions of Myeloma Cells with Bone Marrow Stromal Cells Via $\alpha 4\beta 1$ Integrin-VCAM-1 is Required for the Development of Osteolysis." *Journal of Bone and Mineral Research*, vol. 12, Supp. 1, pp. 104 (Aug. 1997).

(Continued)

*Primary Examiner*—Maher M. Haddad
(74) *Attorney, Agent, or Firm*—Fish & Richardson P.C.

(57) ABSTRACT

Antagonists of alpha 4 integrin/alpha 4 integrin ligand adhesion, which inhibit the biological effects of such adhesion are described and methods for their use are detailed. Such antagonists are useful in suppressing bone destruction associated with multiple myeloma. The homing of multiple myeloma cells to bone marrow and their alpha 4 integrin-dependent release of bone-resorbing factors, resulting in bone destruction in patients with multiple myeloma, is inhibited.

15 Claims, 6 Drawing Sheets

OTHER PUBLICATIONS

Mori et al., "Anti α4 Integrin Antibody Suppresses the Bone Disease of Myeloma and Disrupts Myeloma Marrow Stromal Cell Interactions." *Journal of Bone and Mineral Research*, vol. 14, Supp. 1, pp. 1161 (Sep. 1999).

Mundy, "Pathogenesis of Hypercalcaemia of Malignancy." *Clinical Endocrinology*, vol. 23, No. 1, pp. 705-714 (Jul. 1985).

Mundy et al., "Bone Destruction and Hypercalcemia in Plasma Cell Myeloma." *Seminars in Oncology*, vol. 13, No. 3, pp. 291-299 (Sep. 1986).

Mundy, "Osteopenia." *Disease-a-Month*, vol. 33, No. 10, pp. 537-600 (Oct. 1987).

Garcia-Gilla et al., "Analysis of the activation state of α4β1 integrin in human B cell lines derived from myeloma, leukemia or lymphoma." *FEBS Letters*, vol. 418, No. 3, pp. 337-340 (Dec. 1997).

Barlogie et al., "Extended survival in advanced and refractory multiple . . . ", Jul. 15, 2001, Blood, vol. 98(2):492 (abstract).

Berenson et al., "Long-Term Pamidronate Treatment of Advanced Multiple Myeloma . . . ", Feb. 1998, J. Clin. Oncology, vol. 16 (2):593 (abstract).

Dallas et al., "Ibandronate Reduces Osteolytic Lesions but not Tumor Burden . . . ", Mar. 1, 1998, Blood, vol. 93(5):1697 (abstract).

Damiano et al., "Integrin-Mediated Drug Resistance in Multiple Myeloma", 2000, Leukemia and Lymphama, vol. 38 (1-2):71-81.

Damiano et al., "Cell Adhesion Mediated Drug Resistance (CAM-DR): Role of Integrins . . . ", Mar. 1, 1999, Blood, vol. 93(5):1658-1667.

Mittelman et al., "Erythropoietin induces tumor regression and antitumor . . . ", Aug. 24, 2001, PNAS, vol. 98(9):5181 (abstract).

Mundry et al., "Stromal cells regulate survival of B-lineage leukemic cells . . . ", Sep. 1, 2000, Blood, vol. 96 (5):1926-1932.

Tinhofer et al., "Expression of functional interleukin-15 receptor and autocrine production . . . ", Jan. 15, 2000, Blood, vol. 95 (2):610 (abstract).

Hemler et al., "Characterization of the Cell Surface Heterodimer VLA-4 and Related Peptides", *J. Biol. Chem.* 262:11478-11485, 1987.

Sanchez-Madrid et al., "VLA-3: A novel polypeptide association within the VLA molecular complex: cell distribution and biochemical characterization", *Eur. J. Immunol.* 16:1343-1349, 1986.

Pulido et al., "Functional Evidence for Three Distinct and Independently Inhibitable Adhesion Activities Mediated by the Human Integrin VLA-4", *J. Biol. Chem.* 266:10241-10245, 1991.

Amit et al., "Three-dimensional structure of an antigen-antibody complex at 2.8 A resolution," Science, 233(4765):747-753 (1986).

Rudikoff et al., "Single amino acid substitution altering antigen-binding specificity," Proc. Natl. Acad. Sci. USA, 79(6):1979-83 (Mar. 1982).

Alexanian R. et al., "Treatment for multiple myeloma. Combination chemotherapy with different melphalan dose regimens." JAMA, 208(9):1680-5 (Jun 2, 1969).

Owens, R.J., Young, R.J., "The genetic engineering of monoclonal antibodies," J. Immunol. Methods, 168(2):149-165 (1994).

Alsina, M. et al., "Development of an In Vivo Model of Human Multiple Myeloma Bone Disease," Blood, 87:1495-1501 (1996).

Attal, M. et al., "A Prospective, Randomized Trial of Autologous Bone Marrow Transplantation and Chemotherapy in Multiple Myeloma," N. Engl. J. Med, 335:91-97 (1996).

Atkins C., "Correspondence: High-Dose Chemotherapy in Multiple Myeloma," N. Engl. J. Med., 335:1844 (1996).

Oivanen, T. M. et al., "Correspondence: High-Dose Chemotherapy in Multiple Myeloma," N. Engl. J. Med., 335:1844-1845 (1996).

Attal et al., "Correspondence: High-Dose Chemotherapy in Multiple Myeloma - In Reply," N. Engl. J. Med., 335:1844-1845 (1996).

Bataille, R. et al., "Serum levels of Interleukin 6, a Potent Myeloma Cell Growth Factor, as a Reflect of Disease Severity in Plasma Cell Dyscrasias," J. Clin. Invest., 84:2008-2011 (1989).

Bataille, R. et al., "Mechanisms of Bone Lesions in Multiple Myeloma," Hematology/Oncology Clinics of North America, 6:285-295 (1992).

Bataille, R. et al., "Biologic Effects of Anti-Interleukin-6 Murine Monoclonal Antibody in Advanced Multiple Myeloma," Blood, 86:685-691 (1995).

Seymour, J. F., "Correspondence: Long-Term Pamidronate in Multiple Myeloma," J. Clin. Oncol., 16:2572 (1998).

Berenson, J. R., "Correspondence: Long-Term Pamidronate in Multiple Mteloma - In Reply," J. Clin. Oncol., 16:2572-2573 (1998).

Boyce, B.F. et al., "Bolus Injections of Recombinant Human Interleukin-1 Cause Transient Hypocalcemia in Normal Mice," Endocrinology, 125:2780-2783 (1989).

Chauhan, D. et al., "Regulation of Interleukin 6 in Multiple Myeloma and Bone Marrow Stromal Cells," Stem Cells, 13 (supp. 2):35-39 (1995).

Epstein J., "Myeloma Phenotype: Clues to Disease Origin and Manifestation," Hematology/Oncology Clinics of North America, 6:249-256 (1992).

Garrett, I. R. et al., "A Murine Model of Human Myeloma Bone Disease," Bone, 20:515-520 (1997).

Gosslar, U. et al., "Predominant Role of α4-integrins for distinct steps of lymphoma metastasis," Proc. Natl. Acad. Sci. USA, 93:4821-4826 (1996).

MacDonald, B. R. et al., "Effects of Human Recombinant CSF-GM and Highly Purified CSF-1 on the Formation of Multinucleated Cells with Osteoclast Characteristics in Long-Term Bone Marrow Cultures," J. Bone and Mineral Research, 1:227-233 (1986).

Matsuura, N. et al., "Induction of Experimental Bone Metastasis in Mice by Transfection of Integrin α4β1 into Tumor Cells," AM J. Pathol., 148:55-61 (1996).

Mundy, G.R., "Myeloma Bone Disease," Euro J. Cancer, 34:246-251 (1998).

Oyajobi, B.O. et al., "Expression of Rank Ligand (RankL) by Myeloma Cells Requires Binding to Bone Marrow Stromal Cells Via An α4β1-VCAM-1 Interaction," Second Joint Meeting of the American Society for Bone and Mineral Research and the International Bone and Mineral Society, San Francisco, California: Abstract 1133 (Dec. 4, 1998);Bone, 23(5 Supplement):p. S180 (1998).

Papayannapoulou, T. and Nakamoto, B., "Peripheralization of hemopoietic progenitors in primates treated with anti-VLA$_4$ integrin," Proc. Natl. Acad. Sci. USA 90:9374-9378 (1993).

Qian, F. et al., "Expression of the Integrin α4β1 on Melanoma Cells Can Inhibit the Invasive Stage of Metastasis Formation," Cell, 77:335-347 (1994).

Vanderkerken, K. et al., "Organ Involvement and phenotypic adhesion profile of 5T2 and 5T33 myeloma cells in the C57BL/KaLwRij mouse," Brit. J. Cancer, 76:451-460 (1997).

Roodman, G.D., "Mechanisms of Bone Lesions in Multiple Myeloma and Lymphoma", Database Medline 'Online!: US National Library of Medicine (NLM), Bethesda, MD, US, retrieved from STN, Database accession No. 1998026745, abstract.

Akatsu et al., "Chinese Hamster Ovary Cells Expressing Alpha4beta 1 Integrin Stimulate Osteoclast Formation in Vitro," Database BIOSIS 'Online!: Biosciences Information Service, Philadelphia, PA, US (Aug. 1998) Database accession No. PREV199800429141, abstract.

Michigami et al., "Interactions of Myeloma Cells with Bone Marrow Stromal Cells via Alpha4Beta 1 Integrin - VCAM-1 is required for the Development of Osteolysis," Database SCISEARCH 'Online!, retrieved from STN, Database accession No. 684996.

Mori et al., "Anti-α4 Integrin Antibody Suppresses the Bone Disease of Myeloma and Disrupts Myeloma-marrow Stromal Cell Interactions," Journal of Bone and Mineral Research, 14 Supp. 1, p. S173, Abstract 1161 (1999).

* cited by examiner

METHODS OF TREATING MULTIPLE MYELOMA AND MYELOMA-INDUCED BONE RESORPTION USING INTEGRIN ANTAGONISTS

This is a continuation of PCT application Ser. No. PCT/US99/21170, filed on Sep. 13, 1999, which claims priority from U.S. Provisional Ser. No. 60/100,182, filed Sep. 14, 1998, the contents of which are incorporated herein by reference.

GOVERNMENT RIGHTS

This invention was made with support from the U.S. government under grant number NIH CA40035 awarded by the National Institutes of Health. The government has certain rights in the invention.

FIELD OF THE INVENTION

The present invention relates to a treatment for multiple myeloma, and the release of bone-resorbing factors by myeloma cells, resulting in severe bone loss, which is the major side-effect of myeloma in man. More particularly, this invention relates to integrin antagonists, such as antagonists of alpha4 containing integrins, which inhibit the biological effects of such adhesion, associated with homing of multiple mycloma cells to bone marrow; their subsequent integrin-dependent survival; and their integrin-dependent release of bone-resorbing factors, resulting in bone destruction in patients with multiple myeloma.

BACKGROUND OF THE INVENTION

Multiple myeloma is the second most common hematologic malignancy, with 15,000 new cases diagnosed each year and 30,000 to 40,000 myeloma patients in the U.S. annually (Mundy and Bertolini 1986). Eighty percent of the patients suffer from devastating osteolytic bone destruction caused by increased osteoclast (OCL) formation and activity (Mundy and Bertolini 1986). This bone destruction can cause excruciating bone pain, pathologic fractures, spinal cord compression, and life-threatening hypercalcemia. Because multiple myeloma cannot be cured by standard chemotherapy or stem cell transplantation (Attal et al, 1996), and because of the severe morbidity and potential mortality associated with myeloma bone disease, treatment strategies that control the myeloma growth itself, and in particular the osteolytic bone destruction that occurs in these patients, are vitally important.

However, the pathologic mechanisms responsible for the increased osteoclast activity in patients with multiple myeloma are unknown (Mundy, 1998). The bone lesions occur in several patterns. Occasionally, patients develop discrete osteolytic lesions that are associated with solitary plasmacytomas. Some patients have diffuse osteopenia, which mimics the appearance of osteoporosis, and is due to the myeloma cells being spread diffusely throughout the axial skeleton. In most patients there are multiple discrete lytic lesions occurring adjacent to nests of myeloma cells. Hypercalcemia occurs as a consequence of bone destruction in about one-third of patients with advanced disease. Rarely, patients with myeloma do not have lytic lesions or bone loss, but rather have an increase in the formation of new bone around myeloma cells. This rare situation is known as osteosclerotic myeloma.

Osteolytic bone lesions are by far the most common skeletal manifestations in patients with myeloma (Mundy, 1998). Although the precise molecular mechanisms remain unclear, observations over 15 years have shown that: 1) The mechanism by which bone is destroyed in myeloma is via the osteoclast, the normal bone-resorbing cell; 2) Osteoclasts accumulate on bone-resorbing surfaces in myeloma adjacent to collections of myeloma cells and it appears that the mechanism by which osteoclasts are stimulated in myeloma is a local one; 3) It has been known for many years that cultures of human myeloma cells in vitro produce several osteoclast activating factors, including lymphotoxin-alpha (LT-a), interleukin-1 (IL-1), parathyroid-hormone related protein (PTHrP) and interleukin-6 (IL-6); 4) Hypercalcemia occurs in approximately one-third of patients with myeloma some time during the course of the disease. Hypercalcemia is always associated with markedly increased bone resorption and frequently with impairment in glomerular filtration; 5) The increase in osteoclastic bone resorption in myeloma is usually associated with a marked impairment in osteoblast function. Alkaline phosphatase activity in the serum is decreased or in the normal range, unlike patients with other types of osteolytic bone disease, and radionuclide scans do not show evidence of increased uptake, indicating impaired osteoblast responses to the increase in bone resorption.

Although various mediators listed above have been implicated in the stimulation of osteoclast activity in patients with multiple myeloma, reports of factors produced by myeloma cells have not been consistent, and some studies have been inconclusive due to the presence of other contaminating cell types, including stromal cells and macrophages, in the multiple myeloma cell population. IL-6 is a major myeloma growth factor that enhances the growth of several myeloma cell lines and freshly isolated myeloma cells from patients (Bataille et al., 1989). IL-6 production can be detected in about 40% of freshly isolated myeloma cells by PCR, but only 1 in 150 patients studied show detectable IL-6 production by immunocytochemistry or ELISA assays (Epstein 1992). The IL-6 receptors were only detected in 6 of 13 samples from patients with multiple myeloma (Bataille et al, 1992). Furthermore, mature myeloma cells have been reported to have a minimal proliferative response to IL-6. Interleukin-11 (IL-11) has an IL-6-like activity on plasmacytomas, but to date no one has demonstrated that myeloma cells produce IL-11. Bataille and coworkers (1995) have shown that perfusion of 5 patients with refractory myeloma with an antibody to IL-6 decreased the size of the myeloma cell burden in only 2 of these patients. IL-1 is an extremely potent bone-resorbing agent that induces hypercalcemia in animal models in the absence of renal failure (Boyce et al, 1989). In contrast, hypercalcemia rarely occurs in myeloma patients without renal failure. More importantly, in highly purified myeloma cells, no IL-1 and only rare TNF-a production can be detected, suggesting that other contaminating cell types such as macrophages may be the source of IL-1 and TNF-a (Epstein 1992). Similarly, LT-a is produced by most human myeloma cell lines (Bataille et al, 1995) but does not appear to be produced by mycloma cells in vivo (Alsina et al, 1996). In addition to IL-1, TNF-a, LT-a, and IL-6, myeloma cells produce a truncated form of M-CSF which is biologically active, but M-CSF does not cause hypercalcemia or induce osteoclast formation by itself in human marrow cultures (MacDonald et al, 1986).

Thus, the role of any of these factors in osteolytic bone disease in patients with myeloma has not been clearly demonstrated in vivo, so that known cytokines clearly do not totally account for the bone resorption seen in these patients.

Role of Adhesive Molecule Interactions in Myeloma Bone Disease

Anderson and coworkers were the first group to demonstrate the importance of adhesive interactions between mycloma cells and cells in the marrow microenvironment both in the growth of myeloma cells and the development of osteolytic bone disease. Multiple myeloma cells express cell surface adhesion molecules, CD29 (VLA-4), LFA-1, and CD44 (Chauhan ct al, 1995). These workers suggested that myeloma cells localized to the marrow via specific adhesion interactions between extracellular matrix proteins and bone marrow stromal cells. They further showed that adhesion of multiple myeloma cells to stromal cells triggered IL-6 secretion by both normal and multiple myeloma bone marrow-derived stromal cells and increased IL-6-mediated tumor cell growth. However, antibodies to CD29, LFA-1 or CD44 did not decrease IL-6 production by marrow stromal cells in response to myeloma cells, suggesting that another ligand-receptor interaction triggered the IL-6 secretion by bone marrow stromal cells binding to myeloma cells. Mere identification of a possible adhesion pathway does not necessarily mean that the pathway is important. In this case none of the implicated pathways plays a role in IL-6 production.

Vanderkerken et al (1997) also examined the phenotypic adhesion profile of murine 5T2 cells and 5T33 myeloma cells in a model of murine myeloma. These investigators showed that these cell lines expressed VLA-4, VLA-5, LFA-1, and CD44, and suggested that these adhesive interactions might be important for myeloma cells to bind to marrow stromal cells.

Nevertheless, despite many laboratory advances, the fundamental mechanisms underlying increased osteoclastic bone destruction in myeloma in vivo remain poorly understood. This is reflected in the inability to easily translate the data on adhesive interactions obtained in vitro to the in vivo setting. For example, many in vitro studies implicate both the integrin VLA-4 and the integrin LFA-1 in the adhesion of hematopoietic stem cells to bone marrow stroma (reviewed in Papayannopoulou and Nakamoto, 1993). These in vitro data would predict that either pathway, if blocked in vivo, would result in peripheralization of hematopoietic stem cells from marrow to peripheral blood. Yet, in a primate study, while a monoclonal antibody (mnAb) to VLA-4 effectively peripheralized stem cells, a monoclonal antibody to the beta2 integrin chain of LFA-1 was without effect, despite increasing neutrophil counts, thus demonstrating the efficacy of the mAb (Papayannopoulou and Nakamoto, 1993). These data show that the in vitro results were in fact unable to accurately predict in vivo relevance.

It should be noted that the role of integrin VLA-4 has been studied in metastasis of multiple tumors, including leukemias such as lymphoma, with contradictory results. Thus, transfection of the human alpha 4 chain into Chinese Hamster Ovary (CHO) cells resulted in VLA-4 expression, and rendered these cells able to migrate to bone marrow in vivo, a phenomenon inhibited by mAbs to VLA-4 (Matsuura et al, 1996). In contrast, transfection of lymphoma cells with VLA-4 strongly inhibited metastasis to liver, lung and kidney, and was without effect on homing and proliferation in marrow (Gosslar et al., 1996). In addition, expression of VLA-4 on highly metastatic murine melanoma cells strongly inhibited the formation of pulmonary metastases in vivo (Qian et al., 1994), and did not predispose melanoma to bone marrow metastasis.

In summary it is not clear on the basis of in vitro studies, how to reliably predict in vivo relevance of adhesion pathways. Furthermore, even when in vivo studies have been performed, the resultant data are inconsistent. One major reason for the perplexing inconsistencies in the field of multiple myeloma is that currently available animal models are not good predictors of human disease. In the case of multiple myeloma, human and murine myeloma cell lines which can be grown in vitro rarely are associated with bone destruction in vivo (Mundy 1998).

It would be highly desirable to identify compounds or antagonists which inhibit production of these bone-resorbing factors, thus halting progressive bone destruction and improving the quality of life of patients with myeloma.

SUMMARY OF THE INVENTION

We have used a recently developed murine model of multiple myeloma in which the mouse develops severe osteolysis with all the hallmarks of human disease (Garrett 1997). Using this cell line and animal model we have established that inhibition of the alpha4 integrin/alpha4 integrin ligand pathway in vivo leads to reduced capacitiy for multiple myeloma cells to proliferate and/or survive. We show that cell-cell attachment between myeloma cells and marrow stromal cells via the VLA-4/VCAM-1 interaction is required for an increase in the production of an activity which stimulates osteoclastic bone resorption in the bone microenvironment in vitro.

We propose that this interaction is critical to the homing of myeloma cells to the marrow compartment, to their subsequent survival and growth, to ultimately to the progression of myeloma-induced osteolysis. We tested this in the animal model and found that, in vivo, an antagonist of the alpha4 subunit-containing integrin VLA-4 strongly inhibits the production of antibody of the IgG2b subtype. This isotype is the same as that produced by the 5TGM1 cell line, and is an accurate surrogate for the number of myeloma cells in the marrow compartment at any time. Thus, blockade of the VLA-4 pathway strongly inhibits IgG2b production, and by implication, the level of myeloma burden.

One aspect of the invention is a method for the treating multiple myeloma comprising administering to an individual a therapeutically effective amount of a composition comprising an antagonist of an interaction between an integrin with an alpha4 subunit (e.g., VLA-4) and a ligand for this integrin (e.g., VCAM-1). This antagonist can be an alpha4 integrin binding agent or an alpha4 integrin ligand binding agent. Preferred agents arc anti-VLA-4 or anti-alpha4beta7 antibody homologs (human antibody, a chimeric antibody, a humanized antibody and fragments thereof); anti-VCAM-1 antibody homologs (a human antibody, a chimeric antibody, a humanized antibody and fragments thereof); and a small molecule inhibitor of interactions of alpha4 subunit containing integrins with their ligands. The composition can be administered at a dosage so as to provide from about 0.1 to about 20 mg/kg body weight. In particular, the preferred agents can antagonize an interaction: a) of both VLA-4 and alpha4 beta 7 collectively with their respective alpha4 ligands; or b) only of VLA-4 with its alpha4 ligand; or c) only of alpha4beta7 with its alpha4 ligand.

Another aspect of the invention is a method for inhibiting bone resorption associated with tumors of bone marrow, the method comprising administering to a mammal with said tumors an antagonist of an interaction between an alpha4 subunit containing integrin such as VLA-4 and a ligand for this alpha4 subunit containing integrin, such as VCAM-1, in an amount effective to provide inhibition of the bone resorption. This antagonist can be an alpha4 integrin binding agent such as a VLA-4 binding agent or an alpha4 integrin ligand binding agent such as a VCAM-1 binding agent. Preferred agents are anti-VLA-4 or anti alpha4beta7 antibody homologs (human antibody, a chimeric antibody, a humanized antibody and fragments thereof); anti-VCAM-1 antibody homologs (a human antibody, a chimeric antibody, a humanized antibody and fragments thereof); and a small molecule inhibitor of the interaction of alpha4 subunit-containing integrins with their respective alpha4 integrin ligands (e.g, the VCAM-1/VLA-4 interaction). The antagonist can be administered at a dosage so as to provide from about 0.1 to about 20 mg/kg body weight.

Yet another aspect of the invention is a method of treating a subject having a disorder characterized by the presence of osteoclastogenesis, the method comprising administering to the subject an antagonist of an interaction between an alpha4 subunit bearing integrin and a ligand for an alpha4 subunit-bearing integrin, in an amount sufficient to suppress the osteoclastogenesis. Similarly, the antagonist can be a alpha4 binding agent or an alpha4 ligand binding agent. Preferred agents are anti-VLA4 or anti-alpha4beta7 antibody homologs (human antibody, a chimeric antibody, a humanized antibody and fragments thereof); anti-VCAM-1 antibody homologs (a human antibody, a chimeric antibody, a humanized antibody and fragments thereof); and a small molecule inhibitor of the interaction of alpha4 subunit-containing integrins with their respective alpha4 integrin ligands (e.g, the VCAM-1/VLA-4 interaction). The composition can be administered at a dosage so as to provide from about 0.1 to about 20 mg/kg body weight. Unless stipulated otherwise, all references are incorporated herein by reference.

Figure 1:
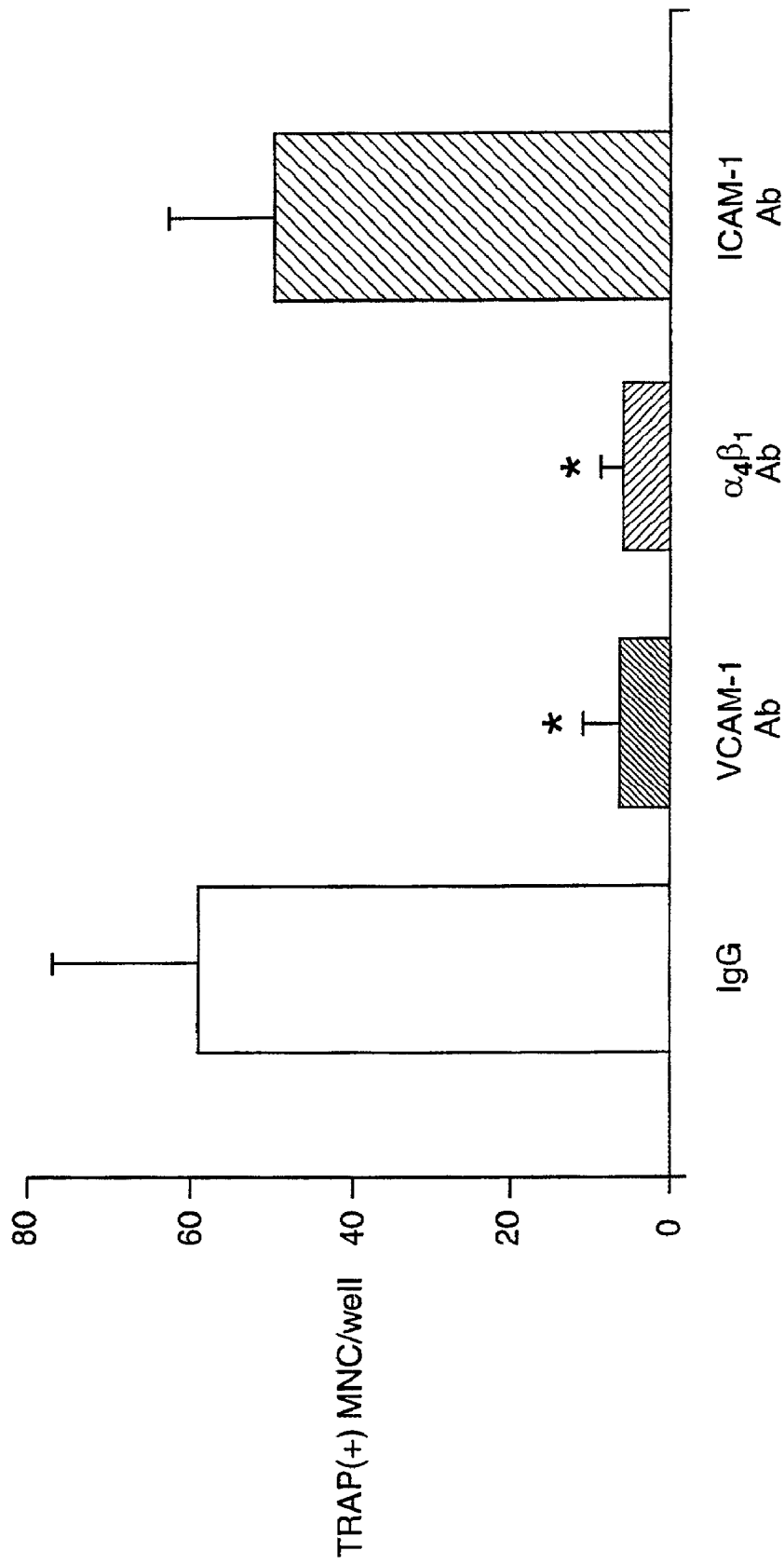
FIG. 1.

Effect of Neutralizing Antibodies on TRAP-positive Multinucleated OC-like Cell Formation in the Co-cultures of 5TGM1 cells and Bone Marrow Cells.

A mixture of 5TGM1 cells (1 e 3) and marrow cells (1 e 6) in suspension was plated in 48-well culture plates and cultured with or without 10 ug/ml anti-VCAM-1 antibody (VCAM-1 Ab), anti-alpha4beta1 antibody ($\alpha4\beta11Ab$), anti-ICAM-1 antibody (ICAM-1 Ab) or rat IgG as a control. After 6 days of culture, cultures were fixed and the number of TRAP-positive multinucleated OC-like cells (TRAP(+) MNC) determined. Both VCAM-1 Ab and alpha4beta1 Ab inhibited TRAP(+) MNC formation, while ICAM-1 Ab had no effect. Data are expressed as mean±S.E. (n=3).*=Significantly different from IgG control.

FIG. 2

Effect of 5TGM1 and ST2 Conditioned Media on bone resorption in Organ Cultures of Fetal Rat Long Bones.

Conditioned media (48 hours) obtained from ST2 alone, 5TGM1 alone, and co-cultures of ST2 and 5TGM1 were assayed for bone resorbing activity in organ cultures of 45 calcium-labeled fetal rat long bones. Labeled fetal rat long bones were cultured in the presence of conditioned media (40%v/v) or control medium for 120 hours. Data are expressed as percentage increase of calcium release over than in the control medium. Release from conditioned medium of ST2 stromal cells is shown as the open bar. Release from 5TGM1 is the hatched bar. Release from conditioned medium harvested from co-culture of 5TGM1 and ST2 is the closed bar. Data are expressed as mean+S.E. (n=4). *=significantly different from ST2 alone. significantly different from 5TGM1 alone.

FIG. 3

Effect of Recombinant Soluble VCAM-1 (sVCAM-1) on the Production of Osteoclastogenic Activity by 5TGM1 Cells.

Conditioned medium was harvested from 5TGM1 cells cultured in the presence or absence of sVCAM-1 ($1\times10^{-8}$ to $1\times10^{-7}$ Molar) for 24 hours. Osteoclastogenic activity of these conditioned media was assayed in the mouse marrow cultures. Bone marrow cells (1e6/well) were plated into 48-well plates, and cultured in the presence of conditioned media (hatched bars) or control medium (IMDM) containing the same concentrations of 5VCAM-1 (open bars). After 6 days, cultures were fixed and the number of TRAP-positive multinucleated OC-like cells (TRAP+MNC) was determined. Conditioned medium from 5TGM1 cells treated with $1\times10^{-7}$ M sVCAM-1 increased TRAP(+)MNC formation. Data are expressed as mean±S.E. (n=3). *=significantly different from controls.

FIG. 4

Effect of mAb PS2 to VLA-4 on serum IgG2b elevation in 5TGM1-bearing mice

Mice were injected with 1e5 5TGM1 cells, which were allowed to colonize the bone marrow. Mice were split into two groups of three, one serving as a control group, and the second treated on days 8, 11, 14, 17, and 20 with 80 ug mAb PS/2 (~4 mg/kg). Levels of IgG2b, the antibody isotype produced by 5TGM1 myeloma cells, were measured weekly from weeks 1 to 6. Mab treatment strongly inhibited IgG2b production, indicative of inhibition of myeloma cell survival and growth in vivo.

FIG. 5

Effect of mAb M/7K-2.7 to VCAM-1 on serum IgG2b elevation in 5TGM1-bearing mice

Figure 4:
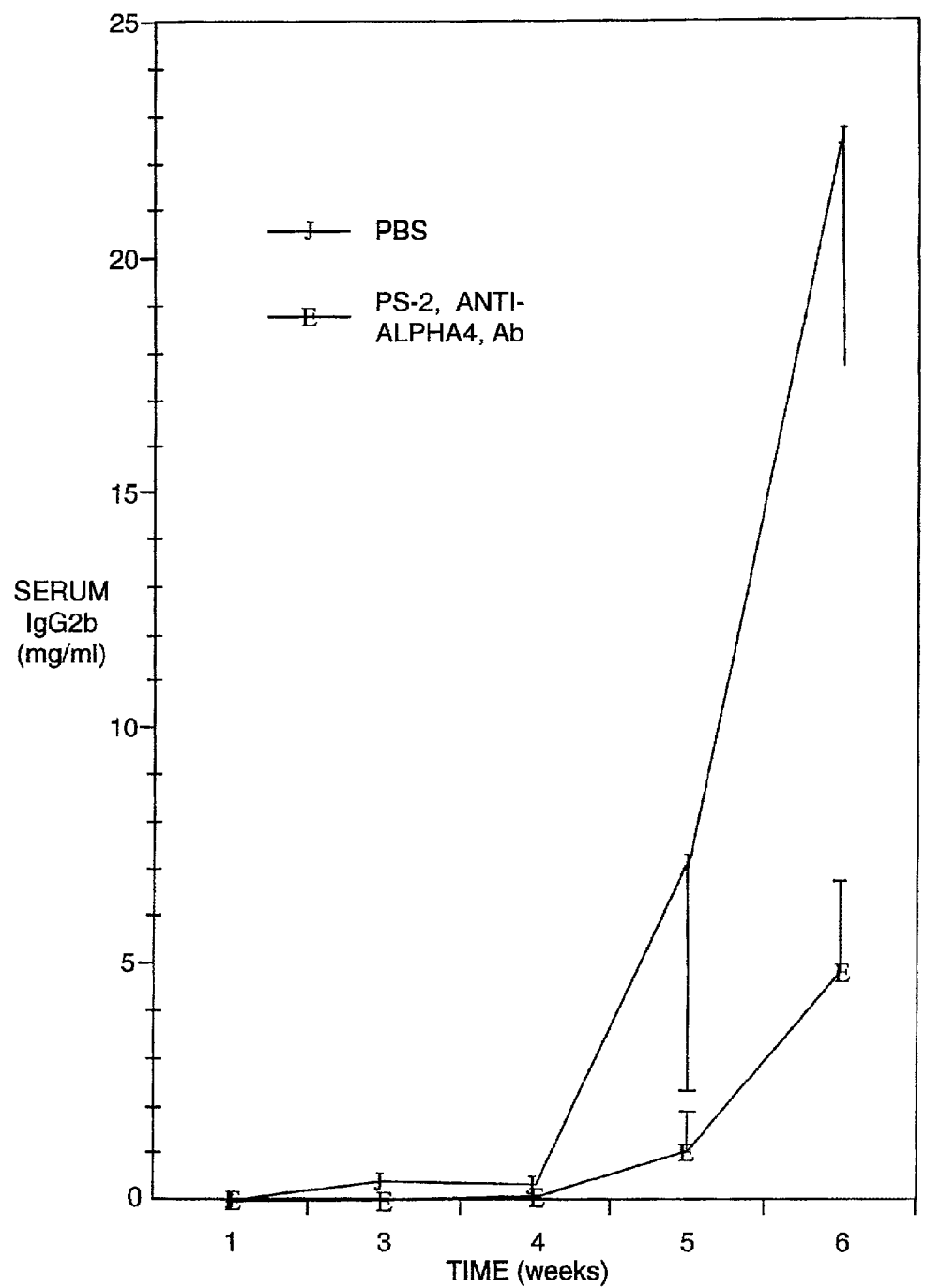

Mice were injected with 5TGM1 cells as described in FIG. 4, which were allowed to colonize the bone marrow. Mice were split into groups of four or five, one group serving as a control group (open square), the second/third groups treated prophylactically at 80 ug (open diamonds) and 160 ug mAb (open circles) (~4 to 8 mg/kg), the fourth group treated therapeutically at 160 ug mAb (triangles). Levels of IgG2b, the antibody isotype produced by 5TGM1 myeloma cells, were measured. Mab treatment strongly inhibited IgG2b production, indicative of inhibition of myeloma cell survival and growth in vivo.

Figure 6:
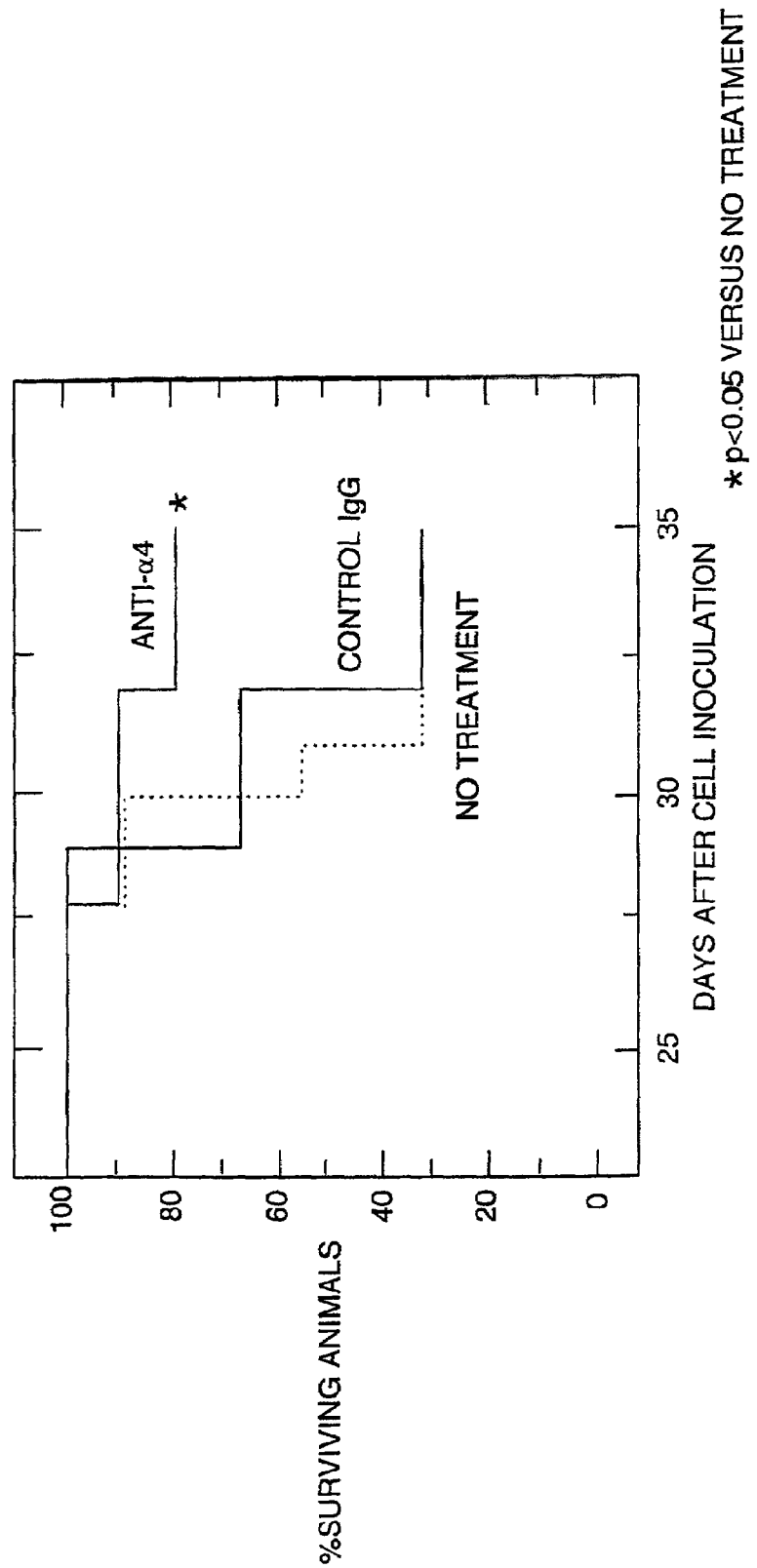

FIG. 6 Effect of anti-alpha4 Integrin Antibody on Survival of Multiple Myeloma-bearing Mice

DETAILED DESCRIPTION OF THE INVENTION

The invention relates to treatments for, among other things, preventing multiple mycloma. More particularly, methods of the invention relate to the use of antagonists of an interaction between an integrin containing an alpha4 subunit and a ligand for this integrin in the treatment of multiple myeloma. The term "multiple myeloma" is intended to mean a medical condition in an individual having a neoplastic disease of plasma cells, with the neoplastic clone representing cells at different stages in the plasma cell lineage from patient to patient (Mundy, 1998).

Alpha 4 beta 1 integrin is a cell-surface receptor for VCAM-1, fibronectin and possibly other molecules that bind with, or otherwise interact with, alpha 4 beta 1 integrin. In this regard, such molecules that bind with, or otherwise interact with, alpha 4 subunit containing integrin are individually and collectively referred to as "alpha4 ligand(s)"). The term a4b1 integrin ("VLA-4" or "a4b1" or "a4b1 integrin", used interchangeably) herein thus refers to polypeptides which are capable of binding to VCAM-1 and members of the extracellular matrix proteins, most particularly fibronectin, or homologs or fragments thereof, although it will be appreciated by workers of ordinary skill in the art that other ligands for VLA-4 may exist and can be analyzed using conventional methods.

Nevertheless, it is known that the alpha4 subunit will associate with other beta subunits besides beta1 so that we may define the term "alpha 4 integrin" as being those integrins whose alpha4 subunit associates with one or another of the beta subunits. A further example of an "alpha4" integrin is alpha4beta7 (R. Lobb and M Hemler, 1994). As used herein, the term "alpha4 integrin(s)" means VLA-4, as well as integrins that contain beta 1, beta7 or any other beta subunit.

As discussed herein, the antagonists used in methods of the invention are not limited to a particular type or structure of molecule so that, for purposes of the invention, any agent capable of binding to any integrin containing an alpha 4 subunit such as VLA-4 on the surface of VLA-4 bearing cells and/or alpha4beta7 integrin on the surface of alpha4beta7-bearing cells [see Lobb and Hemler, J. Clin. Invest., 94: 1722–1728 (1994)] and/or to their respective alpha4 ligands such as VCAM-1 and MadCAM, respectively, on the surface of VCAM-1 and MadCAM bearing cells, and which effectively blocks or coats VLA-4 (or alpha4beta7) or VCAM-1 (or MadCAM) (i.e., a "an alpha4 integrin binding agent" and "alpha4 integrin ligand binding agent" respectively), is considered to be an equivalent of the antagonists used in the examples herein.

An integrin "antagonist" includes any compound that inhibits an alpha 4 integrin(s) from binding with an alpha 4 integrin ligand and/or receptor. Anti-integrin antibody or antibody homolog-containing proteins (discussed below) as well as other molecules such as soluble forms of the ligand proteins for integrins are useful. Soluble forms of the ligand proteins for alpha4 integrins include soluble VCAM-1 or collagen peptides, VCAM-1 fusion proteins, or bifunctional VCAM-1/Ig fusion proteins. For example, a soluble form of an alpha4 integrin ligand or a fragment thereof may be administered to bind to integrin, and preferably compete for an integrin binding site on cells, thereby leading to effects similar to the administration of antagonists such as anti-alpha4 integrin (e.g., alpha4 beta7 antibodies and/or VLA-4 antibodies. In particular, soluble alpha4 integrin mutants that bind alpha 4 integrin ligand but do not elicit integrin-dependent signaling are included within the scope of the invention Such mutants can act as competitive inhibitors of wild type integrin protein and are considered "antagonists". Other antagonists used in the methods of the invention are "small molecules", as defined below.

Included within the invention are methods using an agent that antagonizes the action of more than one alpha 4 integrin, such as a single small molecule or antibody homolog that antagonizes several alpha 4 integrins such as VLA-4 and alpha4 beta 7, or other combinations of alpha4 integrins. Also included within the scope of the invention are methods using a combination of different molecules such that the combined activity antagonizes the action of more than one alpha4 integrin, such as methods using several small molecules or antibody homologs that in combination antagonize the alpha 4 intogrins VLA-4 and alpha4 beta 7, or other combinations of integrins.

As discussed herein, certain integrin antagonists can be fused or otherwise conjugated to, for instance, an antibody homolog such as an immunoglobulin or fragment thereof and are not limited to a particular type or structure of an integrin or ligand or other molecule. Thus, for purposes of the invention, any agent capable of forming a fusion protein (as defined below) and capable of binding to alpha4 integrin ligands and which effectively blocks or coats alpha4 beta 7 and/or VLA-4 integrin is considered to be an equivalent of the antagonists used in the examples herein.

For the purposes of the invention an "antagonist of the alpha 4 integrin ligand/alpha4 integrin interaction" refers to an agent, e.g., a polypeptide or other molecule, which can inhibit or block alpha 4 ligand (e.g., VCAM-1) and/or alpha 4 integrin (e.g., alpha4beta7 or VLA-4)-mediated binding or which can otherwise modulate alpha4 ligand and/or alpha4 integrin function, e.g., by inhibiting or blocking alpha4-ligand mediated alpha4 integrin signal transduction or alpha4 ligand-mediated alpha4 ligand signal transduction and which is effective in the treatment of multiple myeloma, preferably in the same manner as are anti-alpha4 integrin antibodies.

Specifically, an antagonist of the VCAM-1/VLA-4 interaction is an agent which has one or more of the following properties: (1) it coats, or binds to, VLA-4 on the surface of a VLA-4 bearing cell (e.g., a myeloma cell) with sufficient specificity to inhibit a VLA-4-ligand/VLA-4 interaction, e.g., the VCAM-1/VLA-4 interaction between bone stromal cells and myeloma cells; (2) it coats, or binds to, VLA-4 on the surface of a VLA-4 bearing cell (i.e., a myeloma cell) with sufficient specificity to modify, and preferably to inhibit, transduction of a VLA-4-mediated signal e.g., VLA-4 NVCAM-1-mediated signaling; (3) it coats, or binds to, a VLA-4 ligand, (e.g., VCAM1) on bone stromal cells with sufficient specificity to inhibit the VLA-4/VCAM interaction; (4) it coats, or binds to, a VLA-4-ligand (e.g., VCAM-1) on bone stromal cells with sufficient specificity to modify, and preferably to inhibit, transduction of VLA-4-ligand mediated VLA-4 signaling, e.g., VCAM-1-mediated VLA-4 signaling. In preferred embodiments the antagonist has one or both of properties 1 and 2. In other preferred embodiments the antagonist has one or both of properties 3 and 4. Moreover, more than one antagonist can be administered to a patient, e.g., an agent which binds to VLAA can be combined with an agent which binds to VCAM-1.

For example, antibodies or antibody homologs (discussed below) as well as soluble forms of the natural binding proteins for VLA-4 and VCAM-1 are useful. Soluble forms of the natural binding proteins for VLA-4 include soluble VCAM-1 peptides, VCAM-1 fusion proteins, bifunctional VCAM-1/Ig fusion proteins, fibronectin, fibronectin having an alternatively spliced non-type m connecting segment, and fibronectin peptides containing the amino acid sequence EILDV or a similar conservatively substituted amino acid sequence. Soluble forms of the natural binding proteins for VCAM-1 include soluble VLA-4 peptides, VLAD fusion proteins, bifunctional VLA-4/Ig fusion proteins and the like. As used herein, a "soluble VLA-4 peptide" or a "soluble VCAM-1 peptide" is an VLA-4 or VCAM-1 polypeptide incapable of anchoring itself in a membrane. Such soluble polypeptides include, for example, VLA-4 and VCAM polypeptides that lack a sufficient portion of their membrane spanning domain to anchor the polypeptide or are modified such that the membrane spanning domain is non-functional. These binding agents can act by competing with the cell-surface binding protein for VLAN or by otherwise altering VLAN function. For example, a soluble form of VCAM-1 (see, e.g., Osborn et al. 1989, Cell, 59: 1203–1211) or a fragment thereof may be administered to bind to VLA-4, and preferably compete for a VLA-4 binding site on myeloma cells, thereby leading to effects similar to the administration of antagonists such as small molecules or anti-VLA-4 antibodies.

In another example, VCAM-1, or a fragment thereof which is capable of binding to VLA-4 on the surface of VLA-4 bearing myeloma cells, e.g., a fragment containing the two N-terminal domains of VCAM-1, can be fused to a second peptide, e.g., a peptide which increases the solubility or the in vivo life time of the VCAM-1 moiety. The second peptide can be a fragment of a soluble peptide, preferably a human peptide, more preferably a plasma protein, or a member of the inununoglobulin superfamily. In particularly preferred embodiments the second peptide is IgG or a portion or fragment thereof, e.g., the human IgG1 heavy chain constant region and includes, at least the hinge, CH2 and CH3 domains.

Other antagonists useful in the methods of the invention include, but are not limited to, agents that mimic the action of peptides (organic molecules called "small molecules") capable of disrupting the alpha4 integrin/alpha4 integrin ligand interaction by, for instance, blocking VLA-4 by binding VLA-4 receptors on the surface of cells or blocking VCAM-1 by binding VCAM-1 receptors on the surface of cells. These "small molecules" may themselves be small peptides, or larger peptide-containing organic compounds or non-peptidic organic compounds. A "small molecule", as defined herein, is not intended to encompass an antibody or antibody homolog. Although the molecular weight of such "small molecules" is generally less than 2000, we don't intend to apply this figure as an absolute upper limit on molecular weight.

For instance, small molecules such as oligosaccharides that mimic the binding domain of a VLA-4 ligand and fit the receptor domain of VLA-4 may be employed. (See, J. J. Devlin et al., 1990, Science 249: 400406 (1990), J. K. Scott and G. P. Smith, 1990, Science 249: 386–390, and U.S. Pat. No. 4,833,092 (Geysen), all incorporated herein by reference. Conversely, small molecules that mimic the binding domain of a VCAM-1 ligand and fit the receptor domain of VCAM-1 may be employed.

Examples of other small molecules useful in the invention can be found in Komoriya et al. ("The Minimal Essential Sequence for a Major Cell Type-Specific Adhesion Site (CS1) Within the Alternatively Spliced Type III Connecting Segment Domain of Fibronectin Is Leucine-Aspartic Acid-Valine", J. Biol. Chem., 266 (23), pp. 15075–79 (1991)). They identified the minimum active amino acid sequence necessary to bind VLA-4 and synthesized a variety of overlapping peptides based on the amino acid sequence of the CS-1 region (the VLA-4 binding domain) of a particular species of fibronectin. They identified an 8-amino acid peptide, Glu-Ile-Leu-Asp-Val-Pro-Ser-Thr, as well as two smaller overlapping pentapeptides, Glu-Ile-Leu-Asp-Val and Leu-Asp-Val-Pro-Ser, that possessed inhibitory activity against fibronectin-dependent cell adhesion. Certain larger peptides containing the LDV sequence were subsequently shown to be active in vivo (T. A. Ferguson et al., "Two Integrin Binding Peptides Abrogate T-cell-Mediated Immune Responses In Vivo", Proc. Natl. Acad. Sci. USA, 88, pp. 8072–76 (1991); and S. M. Wahl et al., "Synthetic Fibronectin Peptides Suppress Arthritis in Rats by Interrupting Leukocyte Adhesion and Recruitment", J. Clin. Invest., 94, pp. 655–62 (1994)). A cyclic pentapeptide, Arg-Cys-Asp-TPro-Cys (wherein TPro denotes 4-thioproline), which can inhibit both VLA-4 and VLA-5 adhesion to fibronectin has also been described. (See, e.g., D. M. Nowlin et al. "A Novel Cyclic Pentapeptide Inhibits Alpha4Beta1 Integrin-mediated Cell Adhesion", J. Biol. Chem., 268(27), pp. 20352–59 (1993); and PCT publication PCT/US91/04862). This pentapeptide was based on the tripeptide sequence Arg-Gly-Asp from FN which had been known as a common motif in the recognition site for several extracellular-matrix proteins.

Examples of other small molecule VLAW inhibitors have been reported, for example, in Adams et al. "Cell Adhesion Inhibitors", PCT US97/13013, describing linear peptidyl compounds containing beta-amino acids which have cell adhesion inhibitory activity. International patent applications WO 94/15958 and WO 92/00995 describe cyclic peptide and peptidomimetic compounds with cell adhesion inhibitory activity. International patent applications WO 93/08823 and WO 92108464 describe guanidinyl-, urea- and thiourea-containing cell adhesion inhibitory compounds. U.S. Pat. No. 5,260,277 describes guanidinyl cell adhesion modulation compounds.

Such small molecules mimetic agents may be produced by synthesizing a plurality of peptides semi-peptidic compounds or non-peptidic, organic compounds, and then screening those compounds for their ability to inhibit the alpha4 integrin/alpha4 integrin ligand interaction. See generally U.S. Pat. No. 4,833,092, Scott and Smith, "Searching for Peptide Ligands with an Epitope Library", Science, 249, pp. 386–90 (1990), and Devlin et al., "Random Peptide Libraries: A Source of Specific Protein Binding Molecules", Science, 249, pp. 40407 (1990).

In other preferred embodiments, the agent that is used in the method of the invention to bind to, including block or coat, cell-surface alpha4 integrin and/or alpha4 integrin ligand is an anti-VLA-4 and/or anti-alpha4beta7 monoclonal antibody or antibody homolog. Preferred antibodies and homologs for treatment, in particular for human treatment, include human antibody homologs, humanized antibody homologs, chimeric antibody homologs, Fab, Fab', F(ab')2 and F(v) antibody fragments, and monomers or dimers of antibody heavy or light chains or mixtures thereof. Monoclonal antibodies against VLA-4 are a preferred binding agent in the method of the invention.

As used herein, the term "antibody homolog" includes intact antibodies consisting of immunoglobulin light and heavy chains linked via disulfide bonds. The term "antibody homolog" is also intended to encompass a protein comprising one or more polypeptides selected from immunoglobulin light chains, immunoglobulin heavy chains and antigen-binding fragments thereof which are capable of binding to one or more antigens. The component polypeptides of an antibody homolog composed of more than one polypeptide may optionally be disulfide-bound or otherwise covalently crosslinked.

Accordingly, therefore, "antibody homologs" include intact immunoglobulins of types IgA, IgG, IgE, IgD, IgM (as well as subtypes thereof), wherein the light chains of the immunoglobulin may be of types kappa or lambda.

"Antibody homologs" also include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful.

As used herein, a "humanized antibody homolog" is an antibody homolog, produced by recombinant DNA technology, in which some or all of the amino acids of a human immunoglobulin light or heavy chain that are not required for antigen binding have been substituted for the corresponding amino acids from a nonhuman mammalian immunoglobulin light or heavy chain.

As used herein, a "chimeric antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain. In another aspect the invention features a variant of a chimeric molecule which includes: (1) a VLA-4 targeting moiety, e.g., a VCAM-1 moiety capable of binding to antigen (i.e., VLA-4) on the surface of VLA-4 bearing myeloma cells; (2) optionally, a second peptide, e.g., one which increases solubility or in vivo life time of the VLA-4 targeting moiety, e.g., a member of the immunoglobulin superfamily or fragment or portion thereof, e.g., a portion or a fragment of IgG, e.g., the human IgG1 heavy chain constant region, e.g., CH2 and CH3 hinge regions; and a toxin moiety. The VLA-4 targeting moiety can be any naturally occurring VLA-4 ligand or fragment thereof, e,g, a VCAM-1 peptide or a similar conservatively substituted amino acid sequence. A preferred targeting moiety is a soluble VCAM-1 fragment, e.g., the N-terminal domains 1 and 2 of the VCAM-1 molecule. The chimeric molecule can be used to treat a subject, e.g., a human, at risk for disorder, e.g., multiple myeloma, characterized by the presence of myeloma cells bearing VLA-4, and preferably activated VLA-4.

As used herein, a "human antibody homolog" is an antibody homolog produced by recombinant DNA technology, in which all of the amino acids of an immunoglobulin light or heavy chain that are derived from a human source.

Methods of Making Anti-VLA-4 Antibody Homologs

The technology for producing monoclonal antibody homologs is well known. Briefly, an immortal cell line (typically myeloma cells) is fused to lymphocytes (typically splenocytes) from a mammal immunized with whole cells expressing a given antigen, e.g., VLA-4, and the culture supernatants of the resulting hybridoma cells are screened for antibodies against the antigen. See, generally, Kohler et at., 1975, Nature, 265: 295–297.

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-VLA-4 antibodies may be identified by immunoprecipitation of 125I-labeled cell lysates from VLA-4-expressing cells. (See, Sanchez-Madrid et al. 1986, Eur. J. Immunol., 16: 1343–1349 and Hemler et al. 1987, J. Biol. Chem., 262, 11478–11485). Anti-VLA-4 antibodies may also be identified by flow cytometry, e.g., by measuring fluorescent staining of Ramos cells incubated with an antibody believed to recognize VLA4 (see, Elices et al., 1990 Cell, 60: 577–584). The lymphocytes used in the production of hybridoma cells typically are isolated from immunized mammals whose sera have already tested positive for the presence of anti-VLA4 antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, arninopterin and thymidine ("HAT medium"). Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively ftised myeloma cells (unfused splenocytes die after several days because they are not transformed). Hybridomas producing a desired antibody are detected by screening the hybridoma culture supernatants. For example, hybridomas prepared to produce anti-VLA-4 antibodies may be screened by testing the hybridoma culture supernatant for secreted antibodies having the ability to bind to a recombinant alpha4-subunit-expressing cell line (see, Elices et al., supra).

To produce anti-VLA-4 antibody homologs that are intact immunoglobulins, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA-4 antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Several mouse anti-VLA-4 monoclonal antibodies have been previously described. See, e.g., Sanchez-Madrid et al., 1986, supra; Hemler et al., 1987, supra; Pulido et al., 1991, J. Biol. Chem., 266 (16), 10241–10245). These anti-VLA-4 monoclonal antibodies such as HP 1/2 and other anti-VLA-4 antibodies (e.g., HP2/1, HP2/4, L25, P4C2, P4G9) capable of recognizing the P chain of VLA-4 will be useful in the methods of treatment according to the present invention. AntiVLA-4 antibodies that will recognize the VLA-4 alpha4 chain epitopes involved in binding to VCAM-1 and fibronectin ligands (i.e., antibodies which can bind to VLA-4 at a site involved in ligand recognition and block VCAM-1 and fibronectin binding) are preferred. Such antibodies have been defined as B epitope-specific antibodies (B1 or B2) (Pulido et al., 1991, supra) and are also anti-VLA-4 antibodies according to the present invention.

Fully human monoclonal antibody homologs against VLA-4 are another preferred binding agent which may block or coat VLA-4 antigens in the method of the invention. In their intact form these may be prepared using in vitro-primed human splenocytes, as described by Boerner et al., 1991, J. Immunol., 147, 86–95. Alternatively, they may be prepared by repertoire cloning as described by Persson et al., 1991, Proc. Nat. Acad. Sci. USA, 88: 2432–2436 or by Huang and Stollar, 1991, J. Immunol. Methods 141, 227–236. U.S. Pat. No. 5,798,230 (Aug. 25, 1998, "Process for the preparation of human monoclonal antibodies and their use") who describe preparation of human monoclonal antibodies from human B cells. According to this process, human antibody-producing B cells are immortalized by infection with an Epstein-Barr virus, or a derivative thereof, that expresses Epstein-Barr virus nuclear antigen 2 (EBNA2). EBNA2 function, which is required for immortalization, is subsequently shut off, which results in an increase in antibody production.

In yet another method for producing fully human antibodies, U.S. Pat. No. 5,789,650 (Aug. 4, 1998, "Transgenic non-human animals for producing heterologous antibodies") describes transgenic non-human animals capable of producing heterologous antibodies and transgenic non-human animals having inactivated endogenous immunoglobulin genes. Endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. One or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous, fully human antibody homolog.

Large nonimmunized human phage display libraries may also be used to isolate high affinity antibodies that can be developed as human therapeutics using standard phage technology (Vaughan et al, 1996). Yet another preferred binding agent which may block or coat VLA-4 antigens in the method of the invention is a humanized recombinant antibody homolog having anti-VLA-4 specificity. Following the early methods for the preparation of chimeric antibodies, a new approach was described in EP 0239400 (Winter et al.) whereby antibodies are altered by substitution of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies which are totally human in composition except for the substituted murine CDRs. Such CDR-substituted antibodies would be predicted to be less likely to elicit an immune response in humans compared to chimeric antibodies because the CDR-substituted antibodies contain considerably less non-human components. The process for humanizing monoclonal antibodies via CDR "grafting" has been termed "reshaping". (Riechmann et al., 1988, Nature 332, 323–327; Verhoeyen et al., 1988, Science 239, 1534–1536).

Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site directed mutagenesis. In the final stage of the process, human constant region gene segments of the desired isotype (usually gamma I for CH and kappa for CL) are added and the humanized heavy and—light chain genes are co-expressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRS, such that CDRs can be interchanged. Such humanized antibody homologs may be prepared, as exemplified in Jones et al., 1986, Nature 321, 522–525; Riechmann, 1988, Nature 332, 323–327; Queen et al., 1989, Proc. Nat. Acad. Sci. USA 86, 10029; and Orlandi et al., 1989, Proc. Nat. Acad. Sci. USA 86, 3833.

Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity. In a number of cases, it appears to be critical to alter residues in the framework regions of the acceptor antibody in order to obtain binding activity Queen et al., 1989 (supra) and WO 90/07861 (Protein Design Labs) have described the preparation of a humanized antibody that contains modified residues in the framework regions of the acceptor antibody by combining the CDRs of a murine MAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. See also Protein Design Labs U.S. Pat. No. 5,693,762.

One may use a different approach (Tempest et al., 1991, Biotechnology 9,266–271) and utilize, as standard, the V region frameworks derived from NEWM and REI heavy and light chains respectively for CDR-grafting without radical introduction of mouse residues. An advantage of using the Tempest et al., approach to construct NEWM and REI based humanized antibodies is that the 3dimensional structures of NEWM and REI variable regions are known from x-ray crystallography and thus specific interactions between CDRs and V region framework residues can be modeled.

Regardless of the approach taken, the examples of the initial humanized antibody homologs prepared to date have shown that it is not a straightforward process. However, even acknowledging that such framework changes may be necessary, it is not possible to predict, on the basis of the available prior art, which, if any, framework residues will need to be altered to obtain functional humanized recombinant antibodies of the desired specificity. Results thus far indicate that changes necessary to preserve specificity and/or affinity are for the most part unique to a given antibody and cannot be predicted based on the humanization of a different antibody.

Preferred antagonists useful in the present invention include chimeric recombinant and humanized recombinant antibody homologs (i.e., intact immunoglobulins and portions thereof) with B epitope specificity that have been prepared and are described in co-pending U.S. patent application Ser. No. 08/004,798, filed Jan. 12, 1993, PCT Publication US94/00266, filed Jan. 7, 1994. The starting material for the preparation of chimeric (mouse V-human C) and humanized anti-VLA-4 antibody homologs may be a murine monoclonal anti-VLA-4 antibody as previously described, a monoclonal anti-VLA-4 antibody commercially available (e.g., HP2/1, Amae International, Inc., Westbrook, Me.), or a monoclonal anti-VLA-4 antibody prepared in accordance with the teaching herein. For example, the variable regions of the heavy and light chains of the anti-VLA-4 antibody HP ½ have been cloned, sequenced and expressed in combination with constant regions of human immunoglobulin heavy and light chains. Such HP ½ antibody is similar in specificity and potency to the murine HP ½ antibody, and may be useful in methods of treatment according to the present invention.

Other preferred humanized anti-VLA4 antibody homologs are described by Athena Neurosciences, Inc. in PCT/US95/01219 (27 Jul. 1995). These humanized anti-VLA-4 antibodies comprise a humanized light chain and a humanized heavy chain. The humanized light chain comprises three complementarity determining regions ([[CDR1]]CDR1, CDR2 and CDR3) having amino acid sequences from the corresponding complementarity determining regions of a mouse 21.6 immunoglobulin light chain, and a variable region framework from a human kappa light chain variable region framework sequence except in at least position the amino acid position is occupied by the same amino acid present in the equivalent position of the mouse 21.6 immunoglobulin light chain variable region framework. The humanized heavy chain comprises three complementarity determining regions (CDR1, CDR2 and CDR3) having amino acid sequences from the corresponding complementarity determining regions of a mouse 21.6 immunoglobulin heavy chain, and a variable region framework from a human heavy chain variable region framework sequence except in at least one position the amino acid position is occupied by the same amino acid present in the equivalent position of the mouse 21.6 immunoglobulin heavy chain variable region framework.

Therapeutic Applications

In this method according to the first aspect of the invention, VLA-4 binding agents, in particular, VCAM fusions and anti-VLA-4 antibody homologs are preferably administered parenterally. The term "parenteral" as used herein includes subcutaneous, intravenous, intramuscular, intra-articular, intra-synovial, intrasternal, intrathecal, intrahepatic, intralesional and intracranial injection or infusion techniques The VLA-4 binding agents are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromiide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, trishydroxymethyl)methylamine and salts with amino acids such as arginine, lysine, and so forth. Also, the basic nitrogen-containing groups can be quateruized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropyleneblock polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. EI addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention, in particular small molecule antagonists of the VLA-4/VCAM-1 interaction, may be given parenterally or orally. If given orally, they can be administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Topically-transdermal patches may also be used. The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

According to another embodiment compositions containing a compound of this invention may also comprise an additional agent selected from the group consisting of corticosteroids, antiinflammatories, immunosuppressants, antimetabolites, and immunomodulators. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); steroids (inhaled, oral or topical) and interferons (immunomodulators).

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-adminisLered.

The dosage and dose rate of the compounds of this invention effective to prevent, suppress or inhibit cell adhesion will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 50 mg/kg body weight per day of the active ingredient compound are useful. Most preferably, the VLA-4 binding agent, if an antibody or antibody derivative, will be administered at a dose ranging between about 0.1 mg/kg body weight/day and about 20 mg/kg body weight/day, preferably ranging between about 0.1 mg/kg body weight/day and about 10 mg/kg body weight/day and at intervals of every 1–14 days. For non-antibody or small molecule binding agents, the dose range should preferably be between molar equivalent amounts to these amounts of antibody. Preferably, an antibody composition is administered in an amount effective to provide a plasma level of antibody of at least 1 mg/ml. Optimization of dosages can be determined by administration of the binding agents, followed by assessment of the coating of VLA-4-positive cells by the agent over time after administered at a given dose in vivo.

Myeloma cells contained in a sample of the individual's peripheral blood (or bone marrow cells) should be probed for the presence of the agent in vitro (or ex vivo) using a second reagent to detect the administered agent. For example, this may be a fluorochrome labelled antibody specific for the administered agent which is then measured by standard FACS (fluorescence activated cell sorter) analysis. Alternatively, presence of the administered agent may be detected in vitro (or ex vivo) by the inability or decreased ability of the individual's cells to bind the same agent which has been itself labelled (e.g., by a fluorochrome). The preferred dosage should produce detectable coating of the vast majority of VLA-4-positive cells. Preferably, coating is sustained in the case of an antibody homolog for a 1–14 day period.

Animal Models:

The animal model has been described in detail (Garrett 1997). Briefly, Radl et al (1988) had described a murine model of myeloma which arose spontaneously in aged C57BL/KaLwRij mice. This condition occurred in approximately 1 in 200 animals as they aged, and led to a monoclonal gammopathy with some of the features of human disease (Radl 1988). To develop a better and more reproducible animal model we have established and subcloned a cell line from this murine myeloma called 5TGM1, and found that it causes lesions in mice characteristic of human myeloma, such as severe osteolysis and the involvement of non-bone organs including liver and kidney (Garrett 1997). Mice inoculated with cultured cells develop disease in a highly predictable and reproducible manner, which includes formation of a monoclonal gammopathy and radiologic bone lesions. Furthermore, some of the mice become hypercalcemic, and the bone lesions are characterized by increased osteoclast activity. Thus, based on histological examination of affected organs in 5TGM1-bearing mice and increased serum levels of 1gG2b, 5TGM1 is defined as a murine myeloma which recapitulates accurately the hallmarks of human disease.

The following examples are intended to further illustrate certain preferred embodiments of the invention and are not intended to be limiting in nature. In the following examples, the necessary restriction enzymes, plasmids, and other reagents and materials may be obtained from commercial sources and cloning, ligation and other recombinant DNA methodology may be performed by procedures well-known in the art.

Example 1

Materials and Methods

5TGM1 Myeloma Cells

5TGM1 myeloma cells were initially derived from a mycloma which arose spontaneously in aged C57BL/KaLwRij mice (Garrett 1997, Vanderkerken 1997). Cells were grown in Isocove's Modified Dulbecco's Medium (IMDM, Life Technologies Inc., Gaithersburg, Md.) supplemented with 10% fetal bovine serum (FBS, Summit, Fort Collins, Co.) and 1% penicillin-streptomycin solution (GIBCO, Grand Island, N.Y.) at 37 C. in 5% CO2 atmosphere. For in vitro experimentation described below, 5TGM1 cells between passage 25 and 30 were used.

Antibodies, Soluble VCAM-1

Neutralizing antibodies against murine VCAM-1 (MIK-2.7), integrin VLA-4 (PS/2), and Intercellular Adhesion Molecule-1 (ICAM-1, YN1/1.7), were kindly gifted by Dr. Kensuke Miyake (Saga Medical University, Saga, Japan). Recombinant soluble VCAM-1 (Lobb et al, 1991), containing the 7 extracellular domains of human VCAM-1, was the gift of Dr. Roy Lobb, Biogen Inc., Cambridge, Mass.

Reverse Transciption-Polymerase Chain Reaction (RT-PCR)

Using RT-PCR, we confirmed expression of VCAM-1 and integrin alpha4 in bone marrow stromal cells and 5TGM1, respectively. Total RNA was prepared from 5TGM1, a primary culture of bone marrow stromal cells and an ST2 marrow stromal cell line (RIKEN Cell Bank, Tsukuba, Japan) by the single-step RNA isolation method using TRIzol reagent (GIBCO). Three ug of RNA was incubated with 50 ng of random hexamer at 70° C. for 10 min and chilled on ice, then converted to first strand cDNA using reverse transcriptase (Perkin-Elmer, Branchburg, N.J.) according to the manufacturers instruction. The primers used for PCR were as follows: murine VCAM-1 5'-primer; 5'-OH-GCTGCGCGTCACCATTGTTCTC-3'-OH [SEQ ID NO: 1]; murine VCAM-1 3'-primer; 5'-OH-ACCACCCTCT-TGAAGCCTTGTG-3'-OH [SEQ ID NO: 2]; murine integrin alpha4 5'-5'-OH-CCCCTCAACACGAACAGATAGG-3'-OH -[SEQ ID NO: 3]; murine integrin alpha4 3'-primer; 5'-OH-GCCTTGTCCTTAGCAACACTGC-3'-OH [SEQ ID NO: 4].

PCR was performed for 30 cycles consisting of 1 min at 94° C., 1 min at 55° C. and 2 min at 72° C. PCR reaction mixture (total 50 ul) contained 10 microliters. First strand cDNA, 50 mM KCl, 10 mM Tris-HCl (pH 8.3), 2 mM $MgCl_2$, deoxy-NTP mix (0.2 mM each), the pair of primers (0.15 micromolar each) and 2 U Taq DNA polymerase (Perkin-Elmer, Branchburg, N.J.). The PCR products were separated on 2.5% agarose gels containing ethidium bromide and visualized under ultraviolet light. The size of the fragments were confirmed by reference to molecular weight markers.

Attachment of 5TGM1 Cells onto Bone Marrow Stromal Cells

For heterotypic cell-cell adhesion assays, ST2 cells (5 e 4/well) were seeded in 48-well culture plates (Costar, Cambridge, Mass.) and cultured 48 h in alphaMEM supplemented with 10% FBS until confluency. 5TGM1 cells (5 e 6) were labeled by incubation with 10 microCi [methyl-3H] thymidine (New England Nuclear) for 24 h at 37° C. in the culture medium. After the ST2 monolayer was formed, it was incubated with 1% bovine serum albumin (BSA, Sigma, St Louis, Mo.) in serum-free alphaMEM for 1 hours and tritium-labeled 5TGM1 cells were plated onto the monolayer. The system was incubated in the absence or presence of antibodies to VCAM-1 or alpha4beta1 integrin at 37° C. for 1 h. Non-adherent cells were removed by washing-with 5% trichloroacetic acid twice and PBS twice, and adherent cells were solubilized in 300 microliters of 0.25 mM NaOH, neutralized with the same volume of 0.25 mM HCl and the radioactivity was determined in a liquid scientillation counter.

Osteoclast Formation Assay in the Co-culture of 5TGM1 and Mouse Bone Marrow Cells Mouse bone marrow cells were obtained from 5-week-old male C57BL mice as described previously (Yoneda 1993). Femurs and tibiae were dissected aseptically and both ends cut off. Bone marrow cells were flushed out, collected and incubated in alphaMEM supplemented with 10% FBS (Hyclone, Logan, Utah.) and 1% penicillin-streptomycin in 100 mm-culture dishes (Becton Dickinson Labware, Bedford, Mass.) at 37° C. for 2 h. Non-adherent cells containing hemopoietic osteoclast precursors and stromal cells were harvested. Bone marrow cells (1 e 6) and STGMl cells (1 e 3) in 300 microliters of the culture medium were plated onto 48-well culture plates (day 0). On day 2, 300 microliters of fresh culture medium was gently added to each well, and on day 4, 300 microliters of spent medium was replaced with the same volume of fresh medium. On day 6, the cultures were fixed and stained for tartrate-resistant acid phosphatase (TRAP) using commercial kits (Sigma). TRAP-positive multinucleated cells with more than 3 nuclei were defined as osteoclast-like (OC-like) cells, and manually counted under microscope. To confirm that these OC-like cells have the capability to resorb bone, 5TGM1 cells and marrow cells were co-cultured on 5×5 mm whale dentine slices in the same condition, and resorption pits formed on these dentine slices were examined by scanning electron microscopy as described (Yoneda 1992).

In some experiments, co-cultures of 5TGM1 myeloma cells and marrow cells were performed using transwell inserts (Becton Dickinson Labware) to prevent direct of IgG2b, the antibody isotype produced by 5TGM1 myeloma cells, were measured weekly from weeks 1 to 6.

Results

Expression of VCAM-1, VLA-4, and Effect of Antibodies Against VCAM-1 and VLA-4 on 5TGM1 Attachment to ST2 Monolayers Using RT-PCR, we confined the expression of VCAM-1 and integrin VLA-4 in bone marrow stromal cells and myeloma cells, respectively. As expected, both the ST2 stromal cell line and primary bone marrow stromal cells expressed VCAM-1, while 5TGM1 did not. In contrast, the 5TGM1 myeloma cells expressed integrin VLA-4, whereas stromal cells did not (data not shown). In addition, both anti-VCAM-1 antibody (10 ug/mi) and VLA-4 antibody (10 ug/ml) partially (50–80%) inhibited the attachment of 5TGM1 cells to ST2 monolayers, showing that VCAM-1 and the VLA-4 integrin expressed on these cells are biologically functional and that these antibodies have neutralizing activity (data not shown).

OC-like Cell Formation in the Coculture of 5TGM1 Myeloma Cells with Mouse Bone Marrow Cells On day 6 of the coculture of 5TGM1 cells and mouse marrow cells, numerous TRAP-positive multinucleated osteoclast-like (OC-like) cells were formed. These OC-like cells exhibited resorption pit formation on dentine slices, demonstrating that these cells were capable of resorbing bone, and possess an osteoclastic phenotype. In experiments using transwell inserts, formation of OC-like cells was observed when 5TGM1 cells were cultured in direct contact with bone marrow cells. In contrast, there was only a marginal number of OC-like cells formed when 5TGM1 cells were separated from marrow cells by the transwell membrane. Thus 5TGM1 cells induce osteoclast formation in mixed marrow cultures, and this induction requires direct cell-cell contact.

Effect of Antibodies Against VCAM-1 and Integrin VLA-4 on OC-like Cell Formation in the Co-culture of 5TGM1 and Marrow Cells Both anti-VCAM-1 antibody (VCAM-1 Ab, 10 ug/ml) and anti VLA-4-integrin antibody (alpha4beta1 Ab, 10 ug/ml) dramatically inhibited OC/ike cell formation. In contrast mAb against ICAM-1, another adhesion molecule on marrow stromal cells implicated in stromal/myeloma interactions, had no effect on OC-like cell formation (FIG. 1).

To determine whether this inhibition by VCAM-1 and VLA-4 mAbs was specific for 5TGM1-induced OC-like cell formation and was not due to cytotoxicity, the effects of these antibodies were examined on OC-like cell formation induced by 1,25 $(OH)_2D_3$, a widely-used stimulator of osteoclastogenesis in mouse bone marrow cell cultures (Takahashi 1988). Neither VCAM-1 Ab nor VLA-4 mAb inhibited OC-like cell formation induced by vitamin D3, which itself had no effect on VCAM-1 expression in stromal cells (data not shown).

Figure 2:
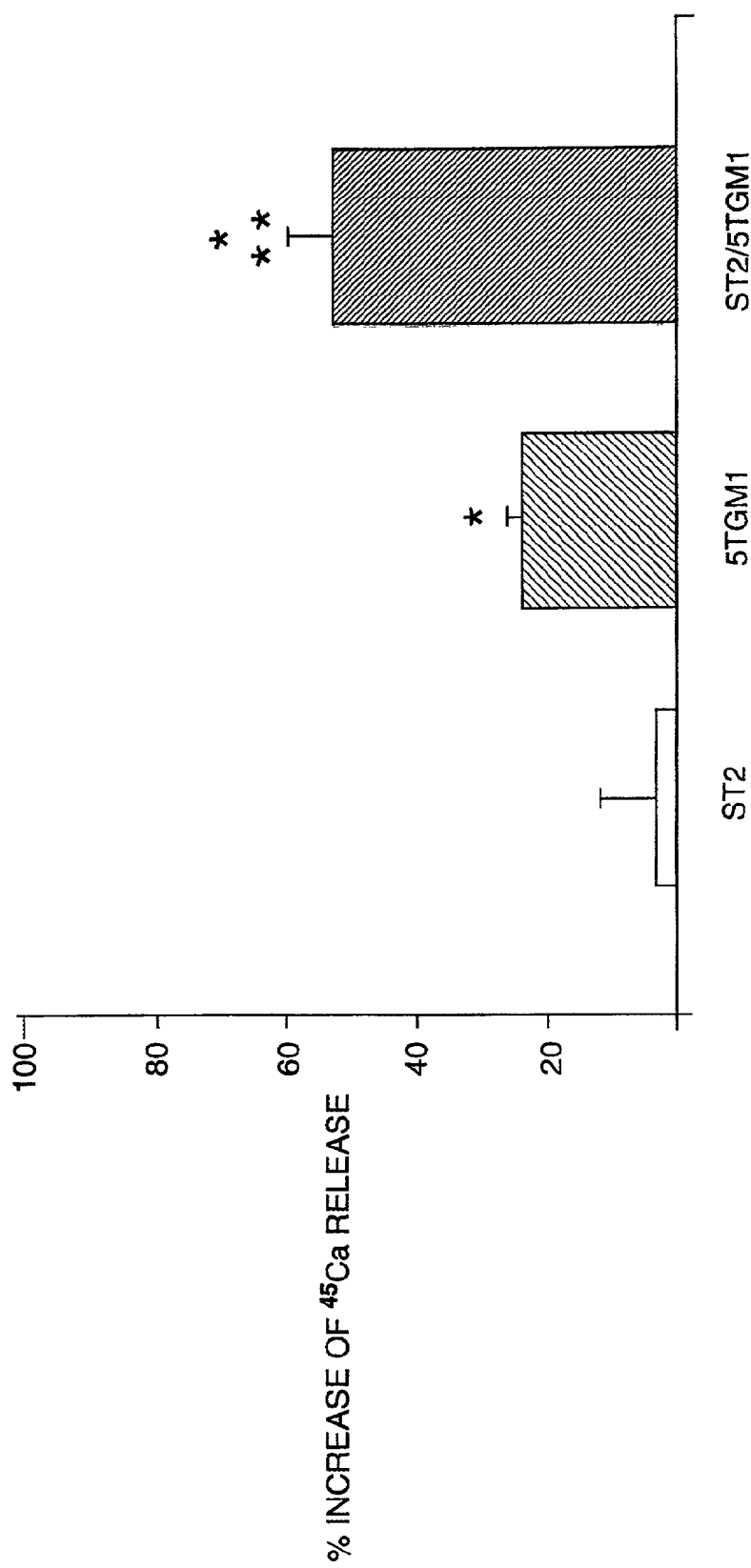

Effect of Conditioned Medium Harvested from the Co-culture of 5TGM1 and ST2 on Bone Resorption Conditioned medium from the coculture of 5TGM1 cells and ST2 cells showed a marked increase in bone resorption in the fetal rat long bone assay (FIG. 2), while conditioned medium of 5TGM1 caused only a marginal increase, s compared to control medium. Conditioned medium from ST2 cells showed no increase in bone resorption. Thus direct cell-cell contact via VCAM-1 and VLA-4 both induces osteoclast-like cells and production of bone-resporboing factors in vitro.

Figure 3:
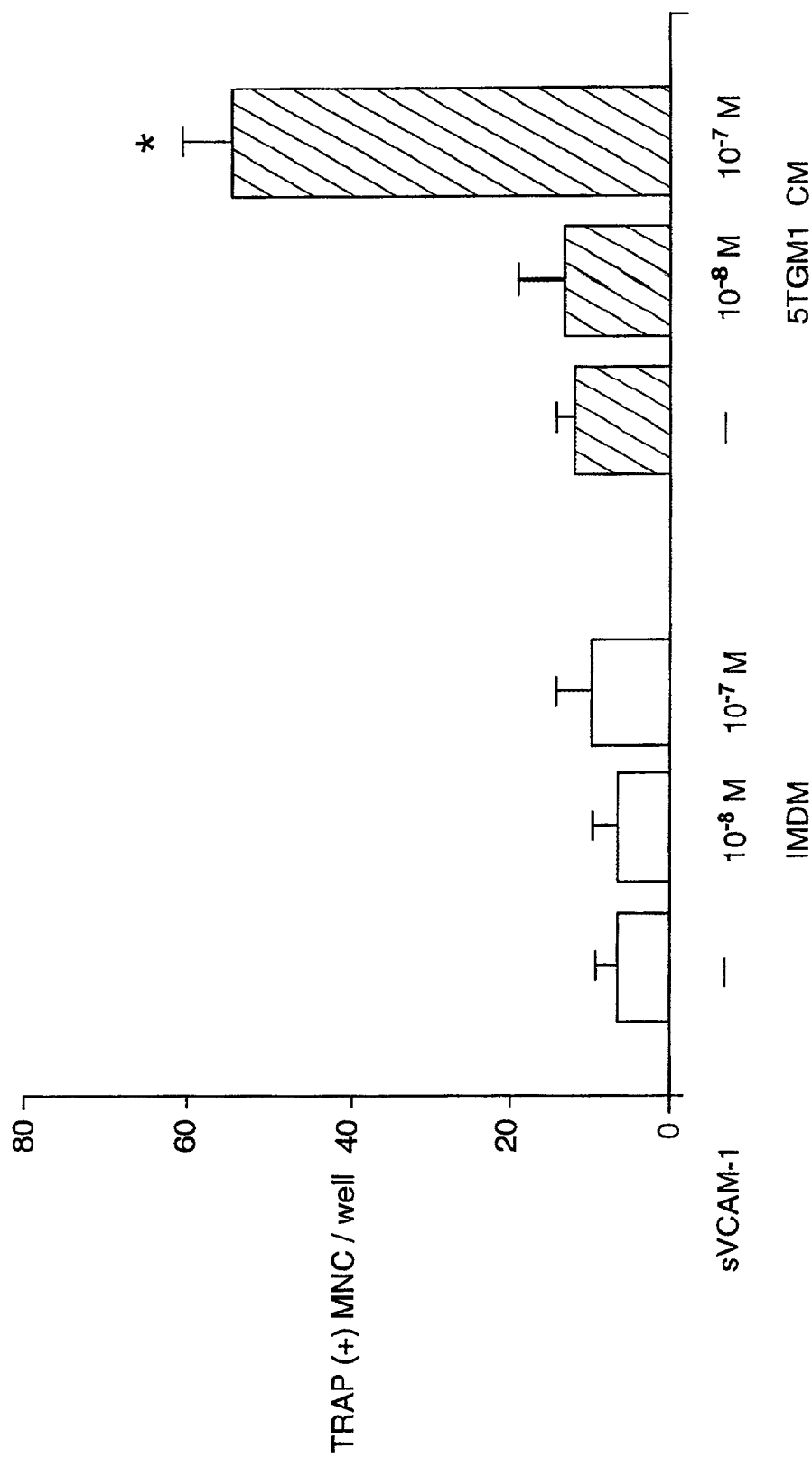

Effect of Recombinant Soluble VCAM-1 (sVCAM-1) on the Production of Bone-resorbing and Osteoclastogenic Activity by 5TGM1 Cells Conditioned medium of 5TGM1 treated with a soluble recombinant form of VCAM-1 (sVCAM-1) increased bone resorption in fetal rat long bones in a dosedependent manner, while conditioned medium obtained from untreated 5TGM1 only marginally increased bone resorption. Soluble VCAM-1 itself had no effects on bone resorption (data not shown). In the mouse marrow culture system, conditioned medium harvested from 5TGM1 cells treated with sVCAM-1 showed increased activity of OC-like cell formation, while conditioned medium of untreated 5TGM1 exhibited only marginal activity of OC-like cell formation (FIG. 3).

Expression of Rank Ligand MRNA in Marrow Stromal Cells (ST2) Cultured in the Presence and Absence of Murine Myeloma Cells Because Rank ligand appears to be an important mediator of OCL formation and may be the final common pathway for the effects of osteoclastogenic cytokines on OCL formation, we have examined the expression of Rank ligand in 5TGM1 and ST2 cells both individually and when cocultured. We find that coculture of 5TGM1 and ST2 cells induces Rank ligand mRNA in the ST2 cells. Furthermore, while 5TGM-1 cells do not expresss Rank ligand, they do so when treated with sVCAM-1 (not shown). Finally, the conditioned medium from 5TGM1 cells treated with sVCAM-1 induced Rank ligand mRNA in ST2 cells, suggesting that the VCAM-1/VLA-4 pathway produces a cytokine in myeloma cells that enhances Rank ligand expression by marrow stromal cells (data not shown).

In summary, we show that 5TGM1 cells alone produce marginal amount of activity that stimulates OC-like cell formation and bone resorption. However, when 5TGM1 myeloma cells were co-cultured with bone marrow cells containing hemopoictic osteoclast precursors and stromal cells, they strongly adhered to the stromal cells and increased OC-like cell formation. There were no OC-like cells formed in the co-cultures in which 5TGM1 cells were prevented from contacting stromal cells. Furthermore, in organ cultures of fetal rat long bones the conditioned medium harvested from the cocultures of 5TGM1 myeloma cells and ST2 bone marrow stromal cells had increased bone resorbing activity compared with conditioned medium of either ST2 or 5TGM1 alone. These data are consistent with the notion that direct cell-cell contact of 5TGM1 cells with bone marrow stromal cells is required for the production of osteoclaststimulating and bone-resorbing activity. We then determined what cell adhesion molecules were involved in the direct cell-cell interaction between 5TGM1 cells and marrow stromal cells that is necessary for the production of osteoclastogenic activity. Our data indicate that VCAM-1 and VLA-4 integrin play a role in this cell-cell interaction, since neutralizing antibodies to these two adhesion molecules profoundly decreased OC-like cell formation in the co-cultures. The VCAM-1/VLA-4 integrin interaction is responsible for the cell-cell communication between marrow stromal cells and 5TGM1 mycloma cells leading to increased production of a osteoclastogenic and bone-resorbing activity. Finally, this bone resorbing activity in part is due to induction of Rank ligand.

Example 2

In Vivo Experiments

Our in vitro studies suggest that the interaction between VLA-4 on myeloma cells with VCAM-1 on marrow stromal cells may play a key role in the induction of bone resorbing activity by myeloma. We have taken the key step of testing this hypothesis in vivo in an animal model which accurately reflects human disease.

A. In this experiment, mice were injected with 1 e 5 5TGM1 myeloma cells, which were allowed to colonize the bone marrow. Mice were split into two groups of three, one serving as a control group, and the second treated biweekly beginning on day 8 with mAb PS/2. Levels of IgG2b, the antibody isotype produced by 5TGM1 myeloma cells, were measured weekly from weeks 1 to 6. Treatment with mAb at a dose of 80 ug per injection (~4 mg/kg) biweekly strongly inhibited IgG2b production, indicative of significant inhibition of myeloma cell survival and growth in vivo (FIG. 4). Further, the treated mice showed reduced incidence of paraplegia (all 3 untreated animals showed paraplegia on day 42, while only one of the treated animals showed paraplegia. The two treated animals with no paraplegia also showed a reduction in spleen and liver weights, which also correlate with tumor burden. Finally, the treated animals showed a reduction in tumor area by histology (from 6.71+/−1.74 to 0.05+/−0.08 square milimeters) in the tibia and femurs. There was no effect of treatment on serum calcium levels (data not shown)

B. In a parallel experiment, treatment with 40 ug PS/2 biweekly had no effect on IgG2b levels (not shown). These data show that mAb PS/2 to VLA-4 strongly inhibits the growth of established myeloma cells in a dose-dependent fashion.

Figure 5:
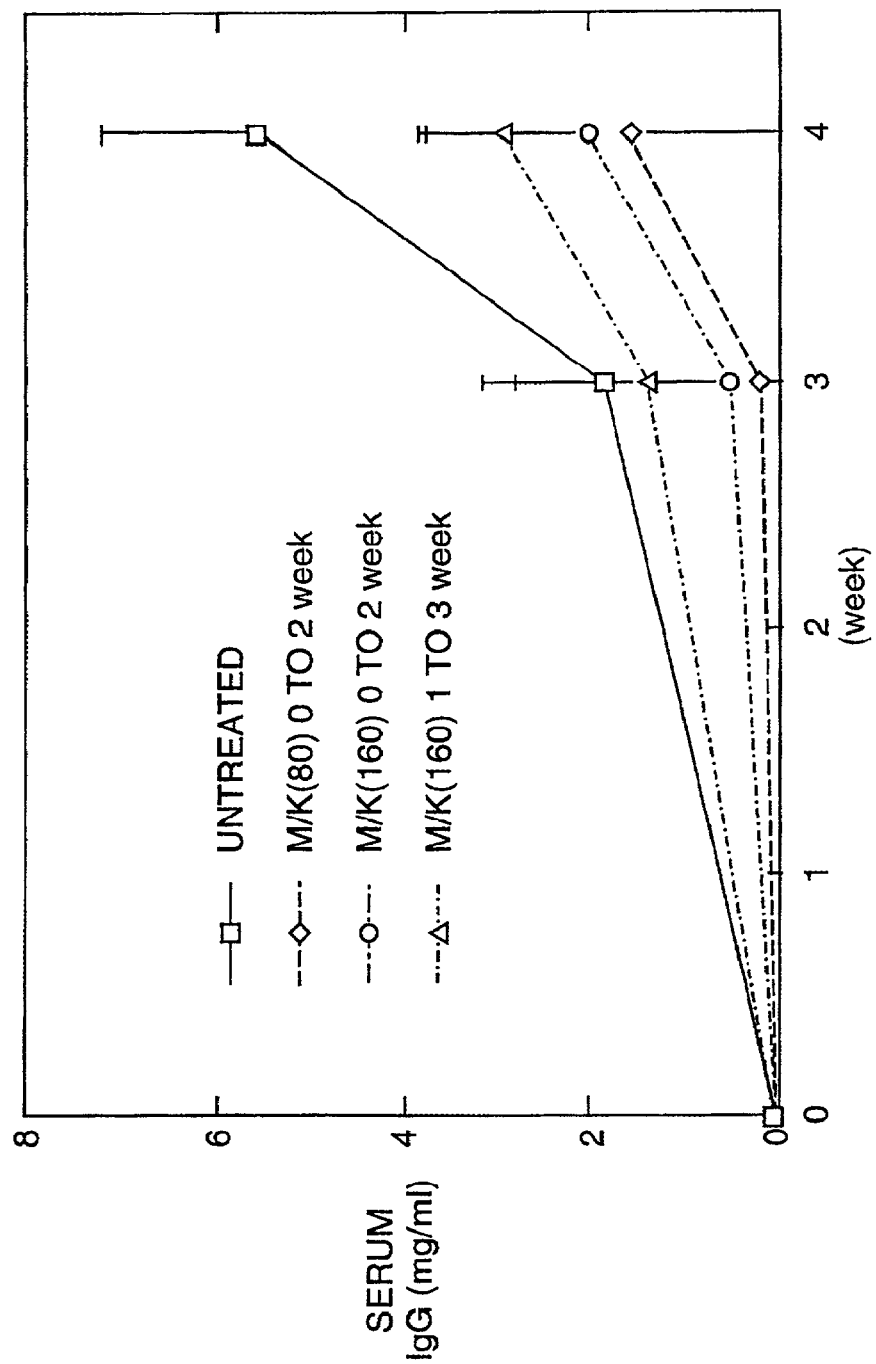

C. In another in vivo experiment, 18 SCID mice were injected with 5TGM1 myeloma cells at day 0. Four mice were treated with PBS; 4 mice were treated in aprophylactic protocol with mAb M/K-2.7 reactive against to mouse VCAM-1 at a dosage of 80 ug (~4 mg/kg) every 3 days starting at day-1 (i.e. days-1, 2, 5, 8, and 11). In a parallel experiment using the same protocol, five mice were treated with 160 ug mAb M/K-2.7. In addition, five mice were treated with 160 ug mAb M/K-2.7 starting at day 8 i.e. days 8, 11, 14, 17, and 20) in a therapeutic protocol. Serum was taken from all mice on days 21, 28, and 35, and animals were X-rayed then sacrificed for histology on day 35. All three treatment groups showed a reduction in serum IgG2b levels, indicative of reduced myeloma cell burden (FIG. 5). A significant effect was also observed on spleen weights at the low dose prophylactic protocol relative to control (0.23+/−0.14 g for control versus 0.08+/−0.04 for treated). In the prophylactic high dose group 4 of 5 animals showed a clear reduction in spleen weight, but the overall value was not significant because of one animal with a large spleen weight (data not presented).

D. One can investigate whether an initial high bolus dose of alpha4 integrin antagonist, followed by a maintenance dose, improves efficacy. The myeloma cells are already established in the marrow compartment, and their tight VLA-4-dependent interaction with VCAM-1 needs to be inhibited. Furthermore, presumably the greater the number of established mycloma cells, the higher the initial dose required to flush cells out into the peripheral circulation.

A larger study with the anti-VLA-4 antibody PS/2 was therefore performed. Twenty eight SCID mice were injected with 5TGM1 mycloma cells at day 0. Nine mice received no treatment; 9 mice received an isotype-matched control IgG mAb; 10 mice were treated with mAb PS/2 to alpha 4 integrin. A different therapeutic regimen was given, in which mice were given a high dose of mAb (200 ug) on days 4,5, and 6, then a maintenance dose of 80 ug (~4 mg/kg) every 3 days starting at day 8.

There was a statistically significant reduction in serum IgG2b when the treated group was compared to either the untreated or control IgG-treated group at weeks 3 and 4 (data not presented). Importantly, when the treated group was compared to either the untreated or control IgG-treated group there was a clear effect on survival (FIG. 6).

Example 3

Other In Vivo Experiments

Based on the information presented herein for the first time, persons having ordinary skill in the art can readily confirm and extend the importance of the alpha4 integrins and their ligands in multiple mycloma using the murine animal model described.

The following series of experiments are well within the level of skill in the art based upon the present disclosure but serve merely to exemplify, and not limit, the types of work.

1) Dose response to mAb PS/2 to determine the optimal biweekly maintenance dose. 80 ug shows good efficacy, but 40 ug was without effect. One examines higher doses up to 20 mg/kg two or three times weekly to determine optimal dosing.
2) Patients present with disease at different stages of severity, linked to increased tumor burden. One examines the efficacy of mab PS/2 given at different times after establishment of disease, i.e. one compares treatment inititation at 8 days (see for example FIG. 4) to initiation after two, three, four and five weeks post inoculation to see how late mAb can be given to provide some relief of symptoms.
3) The effects of mAb MK-2 to murine VCAM-1 are examined, following the same parameters outlined above (dosing, timing of dosing) for mAb to VLA-4. It is anticipated that similar dosing levels will be required to see efficacy.
4) Further markers of myeloma progression are examined, including tumor burden in both marrow and extramedullary sites, quntification of bone lesions by radiographic anaysis of the skeleton by histomorphometry; measurement of rates of bone reportion by evaluation of collagen crosslinks in plasma; measurement of monoclonal protein production in plasma; hypercalcemia where present; and mortality.
5) Multiple myeloma is currently treated inefficiently with standard chemotherapeutic regimens. The additive or synergistic effects of mAbs at optimal dosing in conjunction with, or either before or after, dosing with appropriate chemotherapeutic regimens is examined.
6) The ability of a small molecule alpha4 integrin inhibitor that is selective for one particular alpha4 integrin or is selective for several alpha4 integrins at once or the ability of combinations of such inhibitors, to mimic the effects of mAbs and block myeloma progression is examined using the protocols and outcomes described above. Small molecule inhibitors are delivered parenterally or orally, in the dosing range of 0.1 to 30 mg/kg, once or twice daily, or twice or three times weekly.

ADDITIONAL REFERENCES

Alsina M, Boyce B, Devin R, Anderson J L, Craig F, Mundy G R, Roodman G D. Development of an in vivo model of human multiple myeloma bone disease. Blood 87: 1495–1501, 1996.

Attal M, Harousseau J L, Stoppa A M, Sotto J J, Fuzihet J G, Rossi J F, Casassus P, Maisonneuve H. Facon T, Ifrah N, Payen C, Bataille R. A prospective, randomized trial of autologous bone marrow transplantation and chemotherapy in multiple myeloma. Intergroupe Francais du Myelome. N Engl J Mod 335: 91–97, 1996.

Bataille R, Jourdan M, Zhang X G, Klein B. Serum levels of interleukin-6, a potent myeloma cell growth factor, as a reflection of disease severity in plasma cell dyscrasias. J Clin Invest 84: 2008, 1989.

Bataille R, Chappard D, Klein B. Mechanisms of bone lesions in multiple mycloma. Hem Onc Clin NA 6: 285–295, 1992.

Bataille R, Barlogie B, Lu Z Y, Rossi J F, Lavabre-Bertrand T, Beck T, Wijdenes J, Brochier J, Klein B. Biologic effects of anti-interleukin-6 murine monoclonal antibody in advanced multiple myeloma. Blood 86: 685–691, 1995.

Boyce B F, Yates A J P, Mundy G R. Bolus injections of recombinant human interleukin1 cause transient hypocalcemia in normal mice. Endocrinology 125: 2780–2783, 1989.

Chauhan D. Uchiyama H, Urashima M, Yamamoto K, Anderson K C. Regulation of interleukin-6 in multiple myeloma and bone marrow stromal cells. Stem Cells 13: 35–39, 1995.

Epstein J. Myeloma phenotype: Clues to disease origin and manifestation. Hem Onc Clin NA 6: 249–256, 1992.

Garrett I R, Dallas S, Radl J, Mundy G R: A murine model of human myeloma bone disease. Bone 20: 515–520, 1997.

Gosslar U. Jonas P, Luz A, Lifka A, Naor D, Hamann A, Holzmann B. Predominant role of alpha 4 integrins for distinct steps of lymphoma metastasis. Proc. Natl. Acad. Sci. USA. 93: 4821–4826, 1996.

Lacey D L, Timms E, Tan H L, Kelley M J, Dunstan C R, Burgess T, Elliott R, Colombero A, Elliott G, Scully S, Hsu H, Sullivan J, Hawkins N, Davy E, Capparell C, Eli A, Qian Y X, Kaufman S, Sarosi 1, Shalhoub V, Senaldi G, Guo J, Delaney J, Boyle W J. Osteoprotegerin ligand is a cytokine that regulates osteoclast differentiation and activation. Cell 93: 165–176, 1998.

Lobb R, Chi-Rosso G, Leone D, Rosa M, Newman B, Luhowskyj S, Osborn L, Schiffer S, Benjamin C, Dougas I, Hession C, Chow P. Expression and functional characterisation of a soluble form of vascular cell adhesion molecule 1. Biochem. Biophys. Res. Commun. 178: 1498–1504, 1991.

Lobb, R. and Hemler, M. The Pathophysiologic Role of alpha4 Integrins In Vivo. J. Clin. Invest., 94: 1722–1728 (1994).

MacDonald B R, Mundy G R, Clark S, Wang E A, Kuehl T J, Stanley E R, Roodman G D. Effects of human recombinant CSF-GM and highly purified CSF-1 on the formation of multinucleated cells with osteoclast characteristics in long-term bone marrow cultures. J Bone Min Res 1: 227–233, 1986.

Mbalaviele G, Chen H, Boyce B F, Mundy G R, Yoneda T: The role of cadherin in the generation of multinucleated osteoclasts from mononuclear precursors in murine marrow. J Clin Invest 95: 2757–2765, 1995.

Matsuura N, Puzon-McLaughlin W, Irie A, Morikawa Y, Kakudo K, Takada Y. Induction of experimental bone metastasis in mice by transfection of integrin alpha 4 beta 1 into tumor cells. Am J Pathol 148: 55–61, 1996.

Matsuzaki K, Udagawa N, Takahashi N, Yamaguchi K, Yasuda H, Shima N, Morinaga T, Toyama Y, Yabe Y, Higashio K, Suda T. Osteoclast differentiation factor (ODF) induces osteoclast-like cell formation in human peripheral blood mononuclear cell cultures. Biochem Biophys Res Commun 246: 199–204, 1998.

Mundy G R, Bertolini DR. Bone destruction and hypercalcemia in plasma cell myeloma. Seminar Oncol 3: 291, 1986.

Mundy G R. Myeloma bone disease. Eur. J. Cancer 34: 246–251, 1998.

Papayannopoulou T, Nakamoto B. Peripheralization of hemopoietic progenitors in primates treated with anti-VLA-4 integrin. Proc. Natl. Acad. Sci. USA 90: 9374–9378, 1993.

Qian F, Vaux D L, Weissman I L. Expression of the integrin a4b1 on melanoma cells can inhibit the invasive stage of metastasis formation. Cell, 77: 335–347, 1994.

Radl J, Croese J W, Zurcher C, van den Enden-Vieveen M M, de Leeuw A M. Animal model of human disease. Am. J. Pathol. 132: 593–597, 1988.

Simonet W S, Lacey D L, Dunstan C R, Kelley M, Chang M S, Luthy R, Nguyen H Q, Wooden S, Bennett L, Boone T, Shimamoto G, DeRose M, Elliott R, Colombero A, Tan HL, Trail G, Sullivan J, Davy E, Bucay N, Renshaw-Gegg L, Hughes TM, Hill D, Pattison W, Campbell P, Boyle W J, et al. Osteoprotegerin: a novel secreted protein involved in the regulation of bone density. Cell 309–319, 1997.

Takahashi N, Yamana H, Yoshiki S, Roodman G D, Mundy G R, Jones S H, Boyde A, Suda T: Osteoclast-like cell formation and its regulation by osteotropic hormones in mouse bone marrow cultures. Endocrinology 122: 1373–1382, 1988.

Vanderkerken K, De Raeve H, Goes E, Van Meirvenne S, Radl J, Van Riet 1, Thielemans K, Van Camp B. Organ involvement and phenotypic adhesion profile of 5T2 and 5T33 myeloma cells in the C57BL/KaLwRij mouse. Brit J Cancer 76: 451–460, 1997.

Vaughan T, Williams A J, Pritchard K, Osboum J K, Pope A R, Eamshaw J C, et al. Human antibodies with sub-nanomolar affinities isolated from a large non-immunized phage display library. Nature Biotechnology. 14: 309–314, 1996.

Yasuda H, Shima N, Nakagawa N, Yamaguchi K, Kinosaki M, Mochizuki S, Tomoyasu A, Yano K, Goto M, Murakami A, Tsuda E, Morinaga T, Higashio K, Udagawa N, Takahashi N, Suda T. Osteoclast differentiation factor is a ligand for osteoprotegerin/osteoclastogenesis-inhibitory factor and is identical to TRANCE/RankL. Proc Natl Acad Sci USA 95: 3597–3602, 1998.

Yoneda T, Alsina M M, Garcia J L, Mundy G R: Differentiation of HL-60 Cells into cells with the osteoclast phenotype. Endocrinology 129: 683–689, 1992.

Yoneda T, Lowe C, Lee C H, Gutierrez G, Niewolna M, Williams P, lzbicka E, Uehara Y, Mundy G R: Herbimycin A, a pp60$^{c-src}$ tyrosine kinase inhibitor, inhibits osteoclastic bone resorption in vitro and hypercalcemia in vivo. J Clin Invest 91: 2791–2795, 1993.

The invention claimed is:

1. A method for treating multiple myeloma comprising administering to an individual a therapeutically effective amount of a composition comprising an anti-alpha4 integrin antibody or antigen binding fragment thereof.

2. The method of claim 1, wherein the antibody or antigen binding fragment thereof is an anti-alpha4/beta1 (VLA-4) antibody or antigen binding fragment thereof.

3. The method of claim 1, wherein the anti-alpha4 integrin antibody or antigen binding fragment thereof is selected from the group consisting of a) an antibody or antigen binding fragment thereof that antagonizes the interaction of both VLA-4 and alpha4beta 7 with their respective alpha4 ligands; b) an antibody or antigen binding fragment thereof that antagonizes the interaction of VLA-4 with its alpha4 ligand; and c) an antibody or antigen binding fragment thereof that antagonizes the interaction of alpha4beta7 with its alpha4 ligand.

4. The method of claim 3, wherein the antibody or antigen binding fragment thereof is selected from the group consisting of a human antibody, a chimeric antibody, a humanized antibody and an antigen-binding Fab, Fab', F(ab')$_2$ or F(v) fragment of a human, chimeric or humanized antibody.

5. The method of claim 1, wherein the composition is administered at a dosage so as to provide from about 0.1 to about 20 mg/kg body weight of the antibody or antigen binding fragment thereof.

6. The method of claim 1, wherein the antibody or antigen binding fragment thereof is a human antibody or antigen binding fragment thereof or a humanized antibody or antigen binding fragment thereof.

7. The method of claim 2, wherein the antibody or antigen binding fragment thereof is a human antibody or antigen binding fragment thereof or a humanized antibody or antigen binding fragment thereof.

8. The method of claim 2, wherein the anti-VLA-4 antibody or antigen binding fragment thereof is a humanized anti-VLA-4 antibody or antigen binding fragment thereof.

9. The method of claims 1 or 2, wherein the antibody or antigen-binding fragment thereof is a monoclonal antibody, or antigen-binding fragment thereof.

10. The method of any one of claims 2, 7 and 8, wherein the anti-VLA-4 antibody or antigen-binding fragment thereof binds the alpha chain of VLA-4.

11. The method of any one of claims 2, 7 or 8, wherein the anti-VLA-4 antibody or antigen-binding fragment thereof is a B epitope specific anti-VLA-4 antibody or antigen-binding fragment thereof.

12. The method of any one of claims 1, 2, 3, 4, 5, 6, 7 or 8, wherein the method comprises administering a composition comprising an anti-alpha4 integrin antibody.

13. The method of claim 9, wherein the method comprises administering a composition comprising an anti-alpha4 integrin antibody.

14. The method of claim 10, wherein the method comprises administering a composition comprising an anti-alpha4 integrin antibody.

15. The method of claim 11, wherein the method comprises administering a composition comprising an anti-alpha4 integrin antibody.

* * * * *